(12) United States Patent
el Kaliouby et al.

(10) Patent No.: US 11,465,640 B2
(45) Date of Patent: Oct. 11, 2022

(54) DIRECTED CONTROL TRANSFER FOR AUTONOMOUS VEHICLES

(71) Applicant: Affectiva, Inc., Boston, MA (US)

(72) Inventors: Rana el Kaliouby, Milton, MA (US); Abdelrahman N. Mahmoud, Somerville, MA (US); Taniya Mishra, New York, NY (US); Andrew Todd Zeilman, Beverly, MA (US); Gabriele Zijderveld, Somerville, MA (US)

(73) Assignee: Affectiva, Inc., Boston, MA (US)

( * ) Notice: Subject to any disclaimer, the term of this patent is extended or adjusted under 35 U.S.C. 154(b) by 72 days.

(21) Appl. No.: 16/234,762

(22) Filed: Dec. 28, 2018

(65) Prior Publication Data
US 2019/0152492 A1 May 23, 2019

Related U.S. Application Data

(63) Continuation-in-part of application No. 15/875,644, filed on Jan. 19, 2018, now Pat. No. 10,627,817, (Continued)

(51) Int. Cl.
*B60W 50/08* (2020.01)
*B60W 40/09* (2012.01)
(Continued)

(52) U.S. Cl.
CPC ......... *B60W 50/082* (2013.01); *A61B 5/0013* (2013.01); *A61B 5/0077* (2013.01); (Continued)

(58) Field of Classification Search
CPC .................................................. B60W 50/082
(Continued)

(56) References Cited

U.S. PATENT DOCUMENTS

| 3,034,500 A | 5/1962 | Backster, Jr. |
| 3,548,806 A | 12/1970 | Fisher |

(Continued)

FOREIGN PATENT DOCUMENTS

| JP | 08115367 | 7/1996 |
| KR | 10-2005-0021759 A | 3/2005 |

(Continued)

OTHER PUBLICATIONS

Google Machine Translation for AU patent for AU2017100444A4 ( Feb. 26, 2016) (downloaded 2021).*

(Continued)

*Primary Examiner* — Jean Paul Cass
(74) *Attorney, Agent, or Firm* — Adams Intellex, PLC

(57) ABSTRACT

Techniques are described for cognitive analysis for directed control transfer for autonomous vehicles. In-vehicle sensors are used to collect cognitive state data for an individual within a vehicle which has an autonomous mode of operation. The cognitive state data includes infrared, facial, audio, or biosensor data. One or more processors analyze the cognitive state data collected from the individual to produce cognitive state information. The cognitive state information includes a subset or summary of cognitive state data, or an analysis of the cognitive state data. The individual is scored based on the cognitive state information to produce a cognitive scoring metric. A state of operation is determined for the vehicle. A condition of the individual is evaluated based on the cognitive scoring metric. Control is transferred between the vehicle and the individual based on the state of operation of the vehicle and the condition of the individual.

25 Claims, 13 Drawing Sheets

Related U.S. Application Data which is a continuation-in-part of application No. 15/273,765, filed on Sep. 23, 2016, now abandoned, which is a continuation-in-part of application No. 14/796,419, filed on Jul. 10, 2015, now abandoned, which is a continuation-in-part of application No. 14/460,915, filed on Aug. 15, 2014, now abandoned, which is a continuation-in-part of application No. 13/153,745, filed on Jun. 6, 2011, now abandoned.

(60) Provisional application No. 62/679,825, filed on Jun. 3, 2018, provisional application No. 62/637,567, filed on Mar. 2, 2018, provisional application No. 62/625,274, filed on Feb. 1, 2018, provisional application No. 62/611,780, filed on Dec. 29, 2017, provisional application No. 62/593,440, filed on Dec. 1, 2017, provisional application No. 62/593,449, filed on Dec. 1, 2017, provisional application No. 62/557,460, filed on Sep. 12, 2017, provisional application No. 62/541,847, filed on Aug. 7, 2017, provisional application No. 62/524,606, filed on Jun. 25, 2017, provisional application No. 62/503,485, filed on May 9, 2017, provisional application No. 62/469,591, filed on Mar. 10, 2017, provisional application No. 62/448,448, filed on Jan. 20, 2017, provisional application No. 62/370,421, filed on Aug. 3, 2016, provisional application No. 62/301,558, filed on Feb. 29, 2016, provisional application No. 62/273,896, filed on Dec. 31, 2015, provisional application No. 62/265,937, filed on Dec. 10, 2015, provisional application No. 62/222,518, filed on Sep. 23, 2015, provisional application No. 62/128,974, filed on Mar. 5, 2015, provisional application No. 62/082,579, filed on Nov. 20, 2014, provisional application No. 62/047,508, filed on Sep. 8, 2014, provisional application No. 62/023,800, filed on Jul. 11, 2014, provisional application No. 61/972,314, filed on Mar. 30, 2014, provisional application No. 61/953,878, filed on Mar. 16, 2014, provisional application No. 61/927,481, filed on Jan. 15, 2014, provisional application No. 61/924,252, filed on Jan. 7, 2014, provisional application No. 61/916,190, filed on Dec. 14, 2013, provisional application No. 61/867,007, filed on Aug. 16, 2013, provisional application No. 61/467,209, filed on Mar. 24, 2011, provisional application No. 61/447,464, filed on Feb. 28, 2011, provisional application No. 61/447,089, filed on Feb. 27, 2011, provisional application No. 61/439,913, filed on Feb. 6, 2011, provisional application No. 61/414,451, filed on Nov. 17, 2010, provisional application No. 61/388,002, filed on Sep. 30, 2010, provisional application No. 61/352,166, filed on Jun. 7, 2010.

(51) Int. Cl.

| | | |
|---|---|---|
| *A61B 5/00* | (2006.01) | |
| *G06N 3/00* | (2006.01) | |
| *G06N 20/10* | (2019.01) | |
| *G06K 9/62* | (2022.01) | |
| *G06N 3/04* | (2006.01) | |
| *G06N 7/00* | (2006.01) | |
| *G08G 1/01* | (2006.01) | |
| *A61B 5/18* | (2006.01) | |
| *G08G 1/0967* | (2006.01) | |
| *G06N 3/08* | (2006.01) | |
| *A61B 5/16* | (2006.01) | |
| *B60W 40/08* | (2012.01) | |
| *G06V 20/59* | (2022.01) | |
| *G06V 40/16* | (2022.01) | |
| *G10L 25/63* | (2013.01) | |
| *B60W 50/00* | (2006.01) | |
| *A61B 5/1171* | (2016.01) | |
| *A61B 5/0533* | (2021.01) | |
| *A61B 5/024* | (2006.01) | |

(52) U.S. Cl.
CPC .............. *A61B 5/165* (2013.01); *A61B 5/18* (2013.01); *A61B 5/7267* (2013.01); *B60W 40/08* (2013.01); *B60W 40/09* (2013.01); *G06K 9/6273* (2013.01); *G06N 3/006* (2013.01); *G06N 3/0454* (2013.01); *G06N 3/0481* (2013.01); *G06N 3/084* (2013.01); *G06N 7/005* (2013.01); *G06N 20/10* (2019.01); *G06V 20/597* (2022.01); *G06V 40/166* (2022.01); *G06V 40/176* (2022.01); *G08G 1/0112* (2013.01); *G08G 1/0129* (2013.01); *G08G 1/096716* (2013.01); *G08G 1/096725* (2013.01); *G08G 1/096741* (2013.01); *G08G 1/096775* (2013.01); *A61B 5/02405* (2013.01); *A61B 5/0533* (2013.01); *A61B 5/1176* (2013.01); *A61B 5/4803* (2013.01); *B60W 2040/0827* (2013.01); *B60W 2050/007* (2013.01); *B60W 2420/42* (2013.01); *B60W 2540/26* (2013.01); *B60W 2540/30* (2013.01); *B60W 2900/00* (2013.01); *G10L 25/63* (2013.01)

(58) Field of Classification Search
USPC .......................................................... 701/36
See application file for complete search history.

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,507,291 A | 4/1996 | Stirbl et al. |
| 5,572,596 A | 11/1996 | Wildes et al. |
| 5,619,571 A | 4/1997 | Sandstorm et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,727,124 A * | 3/1998 | Lee ...................... G10L 15/065 |
| | | 704/233 |
| 5,741,217 A | 4/1998 | Gero |
| 5,760,917 A | 6/1998 | Sheridan |
| 5,762,611 A | 6/1998 | Lewis et al. |
| 5,772,508 A | 6/1998 | Sugita et al. |
| 5,772,591 A | 6/1998 | Cram |
| 5,774,591 A | 6/1998 | Black et al. |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini et al. |

(56) References Cited

U.S. PATENT DOCUMENTS

| | | |
|---|---|---|
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,091,334 A | 7/2000 | Galiana et al. |
| 6,092,049 A * | 7/2000 | Chislenko ............ G06Q 30/02 705/7.29 |
| 6,099,319 A | 8/2000 | Zaltman et al. |
| 6,112,186 A * | 8/2000 | Bergh ................ G06Q 30/02 705/7.32 |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ballet et al. |
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |
| 6,629,104 B1 | 9/2003 | Parulski et al. |
| 6,724,920 B1 | 4/2004 | Berenz et al. |
| 6,792,458 B1 | 9/2004 | Muret et al. |
| 6,847,376 B2 | 1/2005 | Engeldrum et al. |
| 6,927,694 B1 * | 8/2005 | Smith ................ B60K 28/066 340/573.1 |
| 7,003,135 B2 | 2/2006 | Hsieh et al. |
| 7,013,478 B1 | 3/2006 | Hendricks et al. |
| 7,027,621 B1 | 4/2006 | Prokoski |
| 7,110,570 B1 | 9/2006 | Berenz et al. |
| 7,113,916 B1 | 9/2006 | Hill |
| 7,120,880 B1 | 10/2006 | Dryer et al. |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,319,779 B1 | 1/2008 | Mummareddy et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |
| 7,428,318 B1 | 9/2008 | Madsen et al. |
| 7,474,801 B2 | 1/2009 | Teo et al. |
| 7,496,622 B2 | 2/2009 | Brown et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,757,171 B1 | 7/2010 | Wong et al. |
| 7,826,657 B2 | 11/2010 | Zhang et al. |
| 7,830,570 B2 | 11/2010 | Morita et al. |
| 7,881,493 B1 | 2/2011 | Edwards et al. |
| 7,921,036 B1 | 4/2011 | Sharma |
| 8,010,458 B2 | 8/2011 | Galbreath et al. |
| 8,022,831 B1 | 9/2011 | Wood-Eyre |
| 8,219,438 B1 | 7/2012 | Moon et al. |
| 8,296,107 B2 * | 10/2012 | Turner ................ G05B 17/02 703/2 |
| 8,300,891 B2 | 10/2012 | Chen et al. |
| 8,369,608 B2 | 2/2013 | Gunaratne |
| 8,401,248 B1 | 3/2013 | Moon et al. |
| 8,442,638 B2 | 5/2013 | Libbus et al. |
| 8,522,779 B2 | 9/2013 | Lee et al. |
| 8,600,120 B2 | 12/2013 | Gonion et al. |
| 8,640,021 B2 | 1/2014 | Perez et al. |
| 8,676,427 B1 * | 3/2014 | Ferguson ............ B60W 10/20 701/23 |
| 8,738,523 B1 | 5/2014 | Sanchez et al. |
| 8,947,217 B2 | 2/2015 | Moussa et al. |
| 9,365,218 B2 * | 6/2016 | Pallett ............... B60W 50/085 |
| 9,478,139 B2 * | 10/2016 | Hsu ..................... G01S 13/931 |
| 9,701,305 B2 * | 7/2017 | Paul .................... B60W 10/04 |
| 9,840,254 B2 * | 12/2017 | Gupta .................. B60W 10/20 |
| 9,873,428 B2 * | 1/2018 | Banvait ............... B60W 30/09 |
| 9,878,738 B2 * | 1/2018 | Klier .................... B62D 6/005 |
| 9,921,581 B2 * | 3/2018 | Tseng .................. G05D 1/0214 |
| 9,940,834 B1 * | 4/2018 | Konrardy ............. G08G 1/161 |
| 10,088,326 B1 * | 10/2018 | Aula .................... G05D 1/0088 |
| 10,126,136 B2 * | 11/2018 | Iagnemma ........... G05D 1/0088 |
| 10,131,362 B1 * | 11/2018 | Gingrich .............. G08B 23/00 |
| 10,156,449 B2 * | 12/2018 | Colijn .................. G01C 21/34 |
| 10,244,094 B2 * | 3/2019 | Iagnemma ............. G08G 1/005 |
| 10,284,317 B1 * | 5/2019 | Sanchez ................ H04H 20/62 |
| 10,309,792 B2 * | 6/2019 | Iagnemma ......... G01C 21/3461 |
| 10,324,463 B1 * | 6/2019 | Konrardy ............. G01S 19/14 |
| 10,331,129 B2 * | 6/2019 | Iagnemma ......... B62D 15/0285 |
| 10,361,802 B1 * | 7/2019 | Hoffberg-Borghesani ................. G11B 27/11 |
| 10,395,332 B1 * | 8/2019 | Konrardy .......... G06F 16/90335 |
| 10,427,684 B1 * | 10/2019 | Ferguson ........ B60W 30/18009 |
| 10,473,470 B2 * | 11/2019 | Iagnemma ............. G01C 21/30 |
| 10,490,078 B1 * | 11/2019 | Fields .................. G08G 1/0129 |
| 10,565,997 B1 * | 2/2020 | Abramovitz ........... G09B 19/06 |
| 10,572,824 B2 * | 2/2020 | Chamberlain ........ G06F 3/0683 |
| 10,580,228 B2 * | 3/2020 | Korchev ............... G07C 5/0808 |
| 10,657,597 B1 * | 5/2020 | Billman ................ G06Q 40/08 |
| 10,681,513 B2 * | 6/2020 | Iagnemma ............. H04W 4/70 |
| 10,846,624 B2 * | 11/2020 | Chamberlain ........ G06F 21/76 |
| 2001/0033286 A1 | 10/2001 | Stokes et al. |
| 2001/0041021 A1 | 11/2001 | Boyle et al. |
| 2002/0007249 A1 | 1/2002 | Cranley |
| 2002/0030665 A1 | 3/2002 | Ano |
| 2002/0042557 A1 | 4/2002 | Bensen et al. |
| 2002/0054174 A1 | 5/2002 | Abbott et al. |
| 2002/0084902 A1 | 7/2002 | Zadrozny et al. |
| 2002/0171551 A1 | 11/2002 | Eshelman |
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0093784 A1 | 5/2003 | Dimitrova et al. |
| 2003/0182123 A1 | 9/2003 | Mitsuyoshi |
| 2003/0191682 A1 | 10/2003 | Shepard et al. |
| 2003/0191816 A1 | 10/2003 | Landress et al. |
| 2004/0181457 A1 | 9/2004 | Biebesheimer |
| 2005/0187437 A1 | 8/2005 | Matsugu |
| 2005/0283055 A1 | 12/2005 | Shirai et al. |
| 2005/0289582 A1 | 12/2005 | Tavares et al. |
| 2006/0011399 A1 | 1/2006 | Brockway et al. |
| 2006/0019224 A1 | 1/2006 | Behar et al. |
| 2006/0143647 A1 | 6/2006 | Bill |
| 2006/0149428 A1 | 7/2006 | Kim et al. |
| 2006/0170945 A1 | 8/2006 | Bill |
| 2006/0235753 A1 | 10/2006 | Kameyama |
| 2007/0167689 A1 | 7/2007 | Ramadas et al. |
| 2007/0173733 A1 | 7/2007 | Le et al. |
| 2007/0239787 A1 | 10/2007 | Cunningham et al. |
| 2007/0255831 A1 | 11/2007 | Hayashi et al. |

(56) References Cited

U.S. PATENT DOCUMENTS

| | | |
|---|---|---|
| 2007/0265507 A1 | 11/2007 | de Lemos |
| 2007/0299964 A1 | 12/2007 | Wong et al. |
| 2008/0059570 A1 | 3/2008 | Bill |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0184170 A1 | 7/2008 | Periyalwar |
| 2008/0208015 A1 | 8/2008 | Morris et al. |
| 2008/0221472 A1 | 9/2008 | Lee et al. |
| 2008/0287821 A1 | 11/2008 | Jung et al. |
| 2008/0292151 A1 | 11/2008 | Kurtz et al. |
| 2009/0002178 A1 | 1/2009 | Guday et al. |
| 2009/0006206 A1 | 1/2009 | Groe |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0133048 A1 | 5/2009 | Gibbs et al. |
| 2009/0150919 A1 | 6/2009 | Lee et al. |
| 2009/0156907 A1 | 6/2009 | Jung et al. |
| 2009/0164132 A1 | 6/2009 | Jung et al. |
| 2009/0193344 A1 | 7/2009 | Smyers |
| 2009/0209829 A1 | 8/2009 | Yanagidaira et al. |
| 2009/0210290 A1 | 8/2009 | Elliott et al. |
| 2009/0217315 A1 | 8/2009 | Malik et al. |
| 2009/0259518 A1 | 10/2009 | Harvey |
| 2009/0270170 A1 | 10/2009 | Patton |
| 2009/0271417 A1 | 10/2009 | Toebes et al. |
| 2009/0285456 A1 | 11/2009 | Moon et al. |
| 2009/0299840 A1 | 12/2009 | Smith |
| 2010/0070523 A1 | 3/2010 | Delgo et al. |
| 2010/0099955 A1 | 4/2010 | Thomas et al. |
| 2010/0134302 A1 | 6/2010 | Ahn et al. |
| 2010/0266213 A1 | 10/2010 | Hill |
| 2010/0274847 A1 | 10/2010 | Anderson et al. |
| 2010/0324437 A1 | 12/2010 | Freeman |
| 2011/0126226 A1 | 5/2011 | Makhlouf |
| 2011/0134026 A1 | 6/2011 | Kang et al. |
| 2011/0143728 A1 | 6/2011 | Holopainen et al. |
| 2011/0144971 A1 | 6/2011 | Danielson |
| 2011/0196855 A1 | 8/2011 | Wable et al. |
| 2011/0231240 A1 | 9/2011 | Schoen et al. |
| 2011/0251493 A1 | 10/2011 | Poh et al. |
| 2011/0263946 A1 | 10/2011 | el Kaliouby et al. |
| 2012/0010867 A1* | 1/2012 | Eder ................... G16H 50/50 703/13 |
| 2012/0089812 A1* | 4/2012 | Smith ................. G06F 15/825 712/21 |
| 2012/0109452 A1 | 5/2012 | Autran et al. |
| 2012/0150430 A1* | 6/2012 | French ............... G01C 21/3453 701/425 |
| 2012/0271484 A1 | 10/2012 | Feit et al. |
| 2012/0324491 A1 | 12/2012 | Bathiche et al. |
| 2013/0023337 A1 | 1/2013 | Bowers et al. |
| 2013/0116587 A1 | 5/2013 | Sommo et al. |
| 2013/0197409 A1 | 8/2013 | Baxter et al. |
| 2013/0204455 A1 | 8/2013 | Chia et al. |
| 2014/0171752 A1 | 6/2014 | Park et al. |
| 2014/0172910 A1 | 6/2014 | Jung et al. |
| 2014/0218187 A1 | 8/2014 | Chun et al. |
| 2015/0213555 A1* | 7/2015 | Barfield, Jr. ............ H04W 4/48 705/4 |
| 2015/0258995 A1 | 9/2015 | Essers et al. |
| 2016/0104486 A1 | 4/2016 | Penilla et al. |
| 2017/0003784 A1 | 1/2017 | Garg et al. |
| 2018/0001184 A1* | 1/2018 | Tran ...................... G06F 1/163 |
| 2018/0050696 A1 | 2/2018 | Misu et al. |
| 2018/0126901 A1* | 5/2018 | Levkova ............ G06K 9/00597 |
| 2018/0173825 A1* | 6/2018 | Ventroux .................. G06F 9/52 |
| 2018/0248895 A1* | 8/2018 | Watson .................... G06N 3/08 |
| 2019/0087691 A1* | 3/2019 | Jelveh .................. G06K 9/6254 |
| 2019/0176837 A1* | 6/2019 | Williams .............. B60W 50/02 |
| 2019/0236447 A1* | 8/2019 | Cohen .................. G05B 13/048 |
| 2019/0385711 A1* | 12/2019 | Shriberg ................. G10L 25/66 |
| 2020/0139977 A1* | 5/2020 | Govindjee .............. B60R 25/25 |
| 2020/0171977 A1 | 6/2020 | Jales Costa et al. |
| 2020/0194123 A1* | 6/2020 | Keohane ................ G16H 50/30 |
| 2020/0285871 A1 | 9/2020 | Tokizaki et al. |
| 2020/0130528 A1 | 10/2020 | Upmanue et al. |

FOREIGN PATENT DOCUMENTS

| | | |
|---|---|---|
| KR | 10-2008-0016303 A | 2/2008 |
| KR | 1020100048688 A | 5/2010 |
| WO | WO 2011/045422 A1 | 4/2011 |

OTHER PUBLICATIONS

Fok, Hing, et al., A Shunting Inhibitory Convolutional Neural Network for Gender Classification, IEEE Xplore, 18th International Conference on Pattern Recognition (ICPR'06), (Aug. 20, 2006)(hereinafter "FOK").*

Fasel, B. (Aug. 2002). Robust face analysis using convolutional neural networks. In Object recognition supported by user interaction for service robots (vol. 2, pp. 40-43). IEEE.

Matsugu, M., Mori, K., Mitari, Y., & Kaneda, Y. (2003). Subject independent facial expression recognition with robust face detection using a convolutional neural network. Neural Networks, 16(5-6), 555-559.

Rana Ayman El Kaliouby, Mind-reading machines: automated inference of complex mental states, Jul. 2005, University of Cambridge, Cambridge, United Kingdom.

International Search Report dated Nov. 14, 2011 for PCT/US2011/39282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

Albiol, Alberto, et al. "Face recognition using HOG-EBGM." Pattern Recognition Letters 29.10 (2008): 1537-1543.

* cited by examiner

DIRECTED CONTROL TRANSFER FOR AUTONOMOUS VEHICLES

RELATED APPLICATIONS

This application claims the benefit of U.S. provisional patent applications "Directed Control Transfer for Autonomous Vehicles" Ser. No. 62/611,780, filed Dec. 29, 2017, "Cognitive State Vehicle Navigation Based on Image Processing" Ser. No. 62/625,274, filed Feb. 1, 2018, "Cognitive State Based Vehicle Manipulation Using Near Infrared Image Processing" Ser. No. 62/637,567, filed Mar. 2, 2018, and "Vehicle Manipulation Using Cognitive State" Ser. No. 62/679,825, filed Jun. 3, 2018.

This application is also a continuation-in-part of U.S. patent application "Vehicle Manipulation using Occupant Image Analysis" Ser. No. 15/875,644, filed Jan. 19, 2018, which claims the benefit of U.S. provisional patent applications "Vehicle Manipulation using Occupant Image Analysis" Ser. No. 62/448,448, filed Jan. 20, 2017, "Image Analysis for Two-sided Data Hub" Ser. No. 62/469,591, filed Mar. 10, 2017, "Vehicle Artificial Intelligence Evaluation of Mental States" Ser. No. 62/503,485, filed May 9, 2017, "Image Analysis for Emotional Metric Generation" Ser. No. 62/524,606, filed Jun. 25, 2017, "Image Analysis and Representation for Emotional Metric Threshold Evaluation" Ser. No. 62/541,847, filed Aug. 7, 2017, "Multimodal Machine Learning for Emotion Metrics" Ser. No. 62/557,460, filed Sep. 12, 2017, "Speech Analysis for Cross-Language Mental State Identification" Ser. No. 62/593,449, filed Dec. 1, 2017, "Avatar Image Animation using Translation Vectors" Ser. No. 62/593,440, filed Dec. 1, 2017, and "Directed Control Transfer for Autonomous Vehicles" Ser. No. 62/611,780, filed Dec. 29, 2017.

The patent application "Vehicle Manipulation using Occupant Image Analysis" Ser. No. 15/875,644, filed Jan. 19, 2018 is also a continuation-in-part of U.S. patent application "Image Analysis in Support of Robotic Manipulation" Ser. No. 15/273,765, filed Sep. 23, 2016, which claims the benefit of U.S. provisional patent applications "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 12, 2015, "Image Analysis Using Sub-Sectional Component Evaluation To Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016.

The patent application "Image Analysis in Support of Robotic Manipulation" Ser. No. 15/273,765, filed Sep. 23, 2016 is a continuation-in-part of U.S. patent application "Mental State Event Definition Generation" Ser. No. 14/796,419, filed Jul. 10, 2015 which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015.

The patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The patent application "Mental State Event Definition Generation" Ser. No. 14/796,419, filed Jul. 10, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014.

The patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The foregoing applications are each hereby incorporated by reference in their entirety.

FIELD OF INVENTION

This application relates generally to cognitive analysis and more particularly to directed control transfer for autonomous vehicles.

BACKGROUND

Many individuals spend substantial amounts of time getting to, waiting for, and traveling in vehicles. Individuals use public transportation networks, such as buses, trains, and airplanes; ride-sharing services such as Uber™ and Lyft™; and personal vehicles; to travel to various destinations. Travel times include daily commuting to and from the office, taking the kids to soccer practice and piano lessons, taking the pets to the veterinary, shopping, traveling, and the many other common activities which require transportation.

Depending on where people live, they use a variety of vehicles to meet their transportation needs. The vehicles can range from cars and motorcycles; to buses, trains and subways; to ride and ride sharing services; and even to unmotorized vehicles such as bicycles. Traveling is time consuming at best, and at worst, boring, frustrating, irritating, and stressful. Rush hour traffic, accidents, inexperienced and incompetent vehicle operators, dangerous vehicle operators, and poorly maintained roads, among other inevitabilities, further complicate vehicular transportation. The difficulties of transportation are also compounded by operating an unfamiliar vehicle, driving in an unfamiliar city, navigating an unfamiliar public transportation network, and even by having to remember to drive on the opposite side of the road. These challenges surrounding transportation can have catastrophic consequences. Irritated operators of vehicles can experience road rage and other antisocial behaviors, while bored, sleepy, tired, impaired, distracted, or inattentive drivers can cause vehicular accidents and injury to themselves, pedestrians, bicyclists, animals, and property.

Transportation generally, and urban transportation particularly, present many design, management, and fiscal problems which can directly impact travelers. Heavily congested surface roads and highways, and woefully insufficient parking, directly influence the cognitive or mental states, moods, and emotions of travelers. The congested roadways cause longer, more dangerous commutes, and the lack of available parking increases the amount of time wasted looking for a place to leave a vehicle. Public transportation, if even available, presents challenges of its own such as overfilled buses, trains, and subways during commuting hours, and underused routes due to lack of interest, poor planning, and other factors. The increased use of bicycles presents its own further challenges when vehicles and bicycles share overfilled roadways that were not originally designed for multi-use scenarios. While vehicle operators and passengers may not be directly involved in the management and financing of transportation systems, they directly experience and suffer from the frustration and annoyance of using the transportation systems, all while carrying the tax burden of paying to build, operate, maintain, and upgrade them.

SUMMARY

Directed control transfer is used for autonomous vehicles. The directed control is based on both a state of operation of the vehicle and a condition of an individual. In-vehicle sensors are used to collect cognitive state data for an individual who is operating a vehicle. The cognitive state data can include facial data, audio data, infrared image data, biosensor data, and so on. The vehicle has various modes of operation that include autonomous, semi-autonomous, and manual modes of operation. One or more processors are used to analyze the cognitive state data collected from the individual. The processors can be within the vehicle or beyond the vehicle. The processors can include handheld electronic devices associated with one or more vehicle occupants. The analysis performed by the one or more processors produces cognitive state information. The cognitive state information includes a subset of the cognitive state data, a summary of the cognitive state data, or an analysis of the cognitive state data. The individual is scored based on the cognitive state information to produce a cognitive scoring metric. The cognitive scoring metric includes a numeric representation for a mental state. The numeric representation includes a probability for occurrence of the mental state. The cognitive state data is used in detection of one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

A state of operation is determined for the vehicle. The state of operation for the vehicle is an autonomous state, a semi-autonomous state, or a manual state. The state of operation for the vehicle includes being in heavy traffic, being on slippery roads, being out of a familiar region, being out of contact with GPS, being in a tunnel, having reached a destination, having reached a distance from a destination, being on a sparsely traveled road, being in a construction zone, being in an earthquake, having an occurrence of a known sound, having an occurrence of an unknown sound, or having a warning occur for a vehicle system. A condition of the individual is evaluated based on the cognitive scoring metric. The condition of the individual includes being alert, engaged, impaired, asleep, unconscious, reclined, drowsy, fatigued, inattentive, or exhibiting antisocial behavior. Control is transferred between the vehicle and the individual based on both the state of operation of the vehicle and the condition of the individual. The transferring control includes transfer of control for the vehicle from the individual to the vehicle in the autonomous mode. The transferring control also includes transfer of control for the vehicle from the vehicle in the autonomous mode back to the individual.

In embodiments, a computer-implemented method for cognitive analysis comprises: collecting, by in-vehicle sensors, cognitive state data for an individual within a vehicle which has an autonomous mode of operation; analyzing, using one or more processors, the cognitive state data collected from the individual to produce cognitive state information; scoring the individual based on the cognitive state information to produce a cognitive scoring metric; determining a state of operation for the vehicle; evaluating a condition of the individual based on the cognitive scoring metric; and transferring control between the vehicle and the individual based on the state of operation of the vehicle and the condition of the individual.

Various features, aspects, and advantages of numerous embodiments will become more apparent from the following description.

BRIEF DESCRIPTION OF THE DRAWINGS

The following detailed description of certain embodiments may be understood by reference to the following figures wherein.

DETAILED DESCRIPTION

Figure 1:
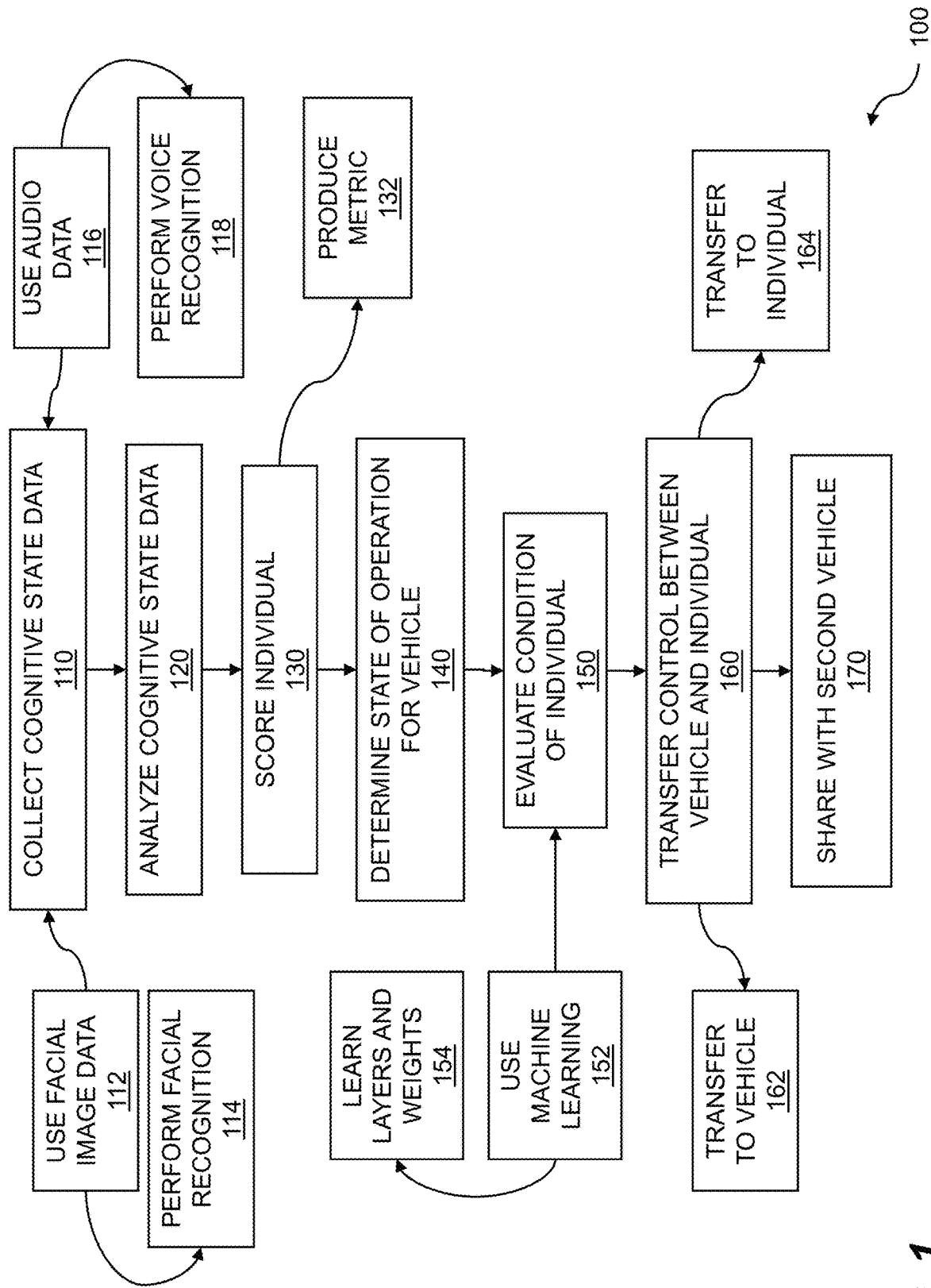
FIG. 1 is a flow diagram for directed control transfer for autonomous vehicles.

Individuals can spend hundreds of hours or more per year getting to, waiting for, and traveling in vehicles. Different types of vehicles can be used, depending on where travelers live, climatic conditions, distances to travel, personal safety, and so on. The vehicles typically include common vehicles such as buses, trains, airplanes, automobiles, ferries, and so on. Other vehicles used include motorcycles, mopeds, bicycles, scooters, etc. For those travelers who do not own a vehicle, who are traveling away from home, or who prefer to let someone else do the driving, ride-sharing services such as Uber™ and Lyft™ have become extremely popular. Annual travel time accumulates when travelers are commuting to and from the office, taking the kids to soccer practice and piano lessons, taking the pets to the veterinary, shopping, traveling, and the many other common activities that require transportation. Travel can become a loathsome activity. For travelers, travel at its best is time consuming, and at worst, boring, frustrating, irritating, stressful, and potentially frightening. Rush hour traffic, accidents, incompetent or dangerous vehicle operators, and badly maintained roads, additionally complicate vehicular transportation. Further transportation difficulties include operating an unfamiliar vehicle, driving in an unfamiliar city or area, navigating a bewildering public transportation network, or even by having to remember to drive on the opposite side of the road. These transportation challenges can have catastrophic consequences and outcomes. Irritated vehicle operators can experience road rage and other antisocial behaviors, while bored, sleepy, tired, impaired, distracted, or inattentive drivers can cause vehicular accidents and injury to themselves, pedestrians, bicyclists, animals, and property Cognitive analysis can be performed for an individual in order to identify a range of cognitive states of the individual. The cognitive states of the individual can be used to understand other states of the individual such as emotional states, mental states, moods, and so on. By understanding the cognitive states of the individual, control of autonomous vehicles can be directed. Further, by determining a state of operation of the vehicle, further decisions can be made regarding directed control transfer. The benefits of directing control transfer for an autonomous vehicle include enhancing the transportation experience for the individual and improving road safety. The enhanced transportation experience for the individual includes autonomous operation, security, or comfort. The road safety improvements derive from aiding the individual who is navigating in foreign surroundings or operating an unfamiliar vehicle, and from preventing a sleepy, impaired, or inattentive individual from operating the vehicle.

In disclosed techniques, a state of operation of a vehicle and a condition of an individual are used for directed control transfer for autonomous vehicles. The state of operation of the vehicle can include being in heavy traffic, being on slippery roads, being out of a familiar region, being out of contact with GPS, being in a tunnel, having reached a destination, having reached a distance from a destination, being on a sparsely traveled road, being in a construction zone, being in an earthquake, having an occurrence of a known sound, having an occurrence of an unknown sound, or having a warning occur for a vehicle system. A condition of the individual can be evaluated. The condition of the individual can include being alert, engaged, impaired, asleep, unconscious, reclined, drowsy, fatigued, inattentive, or exhibiting antisocial behavior. In-vehicle sensors are used for collecting cognitive state data for an individual within a vehicle which has an autonomous mode of operation. The in-vehicle sensors can include one or more cameras, one or more microphones, or one or more biosensors. The one or more cameras can include a video camera, a still camera, a camera array, a plenoptic camera, a web-enabled camera, and so on. The one or more cameras can collect facial data from the individual. A microphone, a transducer, or other audio collection apparatus is used to collect mental state data including audio data and voice data. The one or more biosensors can collect data including heart rate, heart rate variability, electrodermal activity, or heart rate acceleration. One or more processors are used to analyze the cognitive state data collected from the individual to produce cognitive state information. The individual is scored based on the cognitive state information to produce a cognitive scoring metric. The cognitive scoring metric can include a numeric representation for a mental state. The numeric representation can include a probability for occurrence of the mental state. A state of operation is determined for the vehicle. A condition of the individual is evaluated based on the cognitive scoring metric. Control is transferred between the vehicle and the individual based on the state of operation of the vehicle and the condition of the individual.

FIG. 1 is a flow diagram for directed control transfer for autonomous vehicles. Various disclosed techniques include cognitive analysis for transferring control between an autonomous vehicle and an individual. The flow 100 includes collecting, by in-vehicle sensors, cognitive state data 110 for an individual within a vehicle which has an autonomous mode of operation. The in-vehicle sensors can capture image data, audio data, biosensor data, and so on. The in-vehicle sensors can include cameras, microphones, motion sensors, and the like. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. A microphone can include an audio transducer or other audio capture apparatus. The biosensor data can be captured using optical, piezoelectric, or electrochemical sensors; accelerometers; or other sensors. In embodiments, the biosensor data can include heart rate, heart rate variability, electrodermal activity, or acceleration. Other in-vehicle sensors can be used to capture other data from the individual. In embodiments, the in-vehicle sensors include one or more infrared imaging sensors. The infrared imaging sensors can be used to detect an elevated temperature of the individual. The elevated temperature of the individual can be attributable to anger, illness, inebriation, and so on.

In embodiments, the cognitive state data includes facial image data 112 from the individual. The facial image data can be determined by identifying a face within a frame of a video, a still image, etc. The in-vehicle sensors can include a plurality of cameras to capture a multiplicity of views. The facial image data can be enlarged, reduced, rotated, translated, and so on. In embodiments, the multiplicity of views can allow for facial occlusion by one camera from the plurality of cameras. The multiplicity of views can be combined, compared, etc., to obtain an unobstructed view of the face and to perform facial recognition of the individual 114. In further embodiments, the cognitive state data includes audio data 116 from the individual. The audio data can be collected from a plurality of microphones. The audio data can include voice data from the individual. The audio data can include spoken language information, language verbiage, non-speech vocalizations, and the like. The non-speech vocalizations can include grunts, yelps, squeals, snoring, sighs, laughter, filled pauses, unfilled pauses, yawns, etc. Further embodiments include performing voice recognition on the individual 118. The voice recognition of the individual can be used to identify the individual, to enable the individual to access the vehicle, and so on.

The flow 100 includes analyzing, using one or more processors, the cognitive state data 120 that was collected from the individual to produce cognitive state information. The cognitive state data, such as the facial image data, the audio data, and the physiological data, can be used in detection of one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. In embodiments, the cognitive state information can include a subset of the cognitive state data, a summary of the cognitive state data, or an analysis of the cognitive state data. The flow 100 includes scoring the individual 130 based on the cognitive state information to produce a cognitive scoring metric 132. The cognitive scoring metric can include a numeric value, a range of values, text, and so on. In embodiments, the cognitive scoring metric can include a numeric representation for a mental state. A mental state can include sad, happy, stressed, bored, etc. In embodiments, the numeric representation can include a probability for occurrence of the mental state.

The flow 100 includes determining a state of operation for the vehicle 140. The state of operation of the vehicle can include autonomous operation, semi-autonomous operation, manual operation, and so on. In embodiments, the state of operation for the vehicle can include being in heavy traffic, being on slippery roads, being out of a familiar region, being out of contact with GPS, being in a tunnel, having reached a destination, having reached a distance from a destination, being on a sparsely traveled road, being in a construction zone, being in an earthquake, having an occurrence of a known sound, having an occurrence of an unknown sound, or having a warning occur for a vehicle system. The state of operation of the vehicle can be used to determine how autonomous operation or semi-autonomous operation can be conducted, whether such operation should be conducted, and so on. The state of operation of the vehicle can be used to enhance driver aids which can include a visual navigation display, audio aids such as spoken directions, cautions, etc.

The flow 100 includes evaluating a condition of the individual 150 based on the cognitive scoring metric. The cognitive scoring metric can include a numeric representation of a mental state, a mood, an emotional state, and so on. The numerical representation can include a value, a range of values, a probability for occurrence of a given mental state, and so on. In embodiments, the condition of the individual includes being alert, engaged, impaired, asleep, unconscious, reclined, drowsy, fatigued, inattentive, or exhibiting antisocial behavior. The condition of the individual can be used to determine whether the individual should be permitted to operate the vehicle, to set up vehicle performance parameters for the individual, and so on. The flow 100 includes evaluating the condition of the individual based on machine learning 152. The machine learning can be based on a deep neural network, on a deep learning network, etc. In embodiments, the deep learning network can include a convolutional neural network. The convolutional neural network can use an integrated circuit, one or more processors, servers, and so on. In embodiments, the machine learning includes learning layers and weights 154 for a deep learning network. The layers and weights can be applied to the convolutional neural network. In embodiments, the machine learning can be tailored for the individual. The tailoring of the machine learning can be based on an identifier (ID) for the individual, on login credentials, on facial or voice recognition, and so on. The machine learning can be based on a profile for the individual. The profile for the individual can include vehicle preferences, vehicle settings, preferred transportation modes, routes, times for commuting, and so on. The machine learning can be based on historical data for the individual.

The flow 100 includes transferring control between the vehicle and the individual based on the state of operation of the vehicle and the condition of the individual 160. The state of operation of the vehicle can include autonomous operation, semi-autonomous operation, manual operation, and so on. As mentioned above, the state of the vehicle may also include being in heavy traffic, being on weather-affected roads, being in an unfamiliar region, etc. The condition of the individual can also affect the transferring control between the vehicle and the individual. The condition of the individual can include being alert, being impaired, being inattentive, and so on. In embodiments, the transferring control includes transfer of control for the vehicle from the individual to the vehicle 162 in the autonomous mode. The transfer of control from the individual to the vehicle in autonomous mode can be based on a decision by the individual to transfer control to the vehicle. The transfer of control from the individual to the vehicle in autonomous mode can also be based on an output determined by the machine learning. In embodiments, the transferring control includes transfer of control for the vehicle from the vehicle in the autonomous mode to the individual 164. The condition of the individual can be evaluated and the individual can receive transfer of the control of the vehicle. The transfer can be determined by the machine learning when there is an operating condition that requires human intervention of control of the vehicle. The flow 100 includes sharing results of the machine learning with a second vehicle 170. The second vehicle can be a vehicle operated by the individual, a vehicle in which the individual is a passenger, and so on. The second vehicle can be sufficiently similar to the first vehicle such that any setting for the first vehicle can be applied to the second vehicle. The second vehicle can be a fleet vehicle. The second vehicle can be different from the first vehicle. The second vehicle can be an automobile, a truck, a bus, a sport utility vehicle, a van, and so on. Various steps in the flow 100 may be changed in order, repeated, omitted, or the like without departing from the disclosed concepts. Various embodiments of the flow 100 can be included in a computer program product embodied in a non-transitory computer readable medium that includes code executable by one or more processors.

Figure 2:
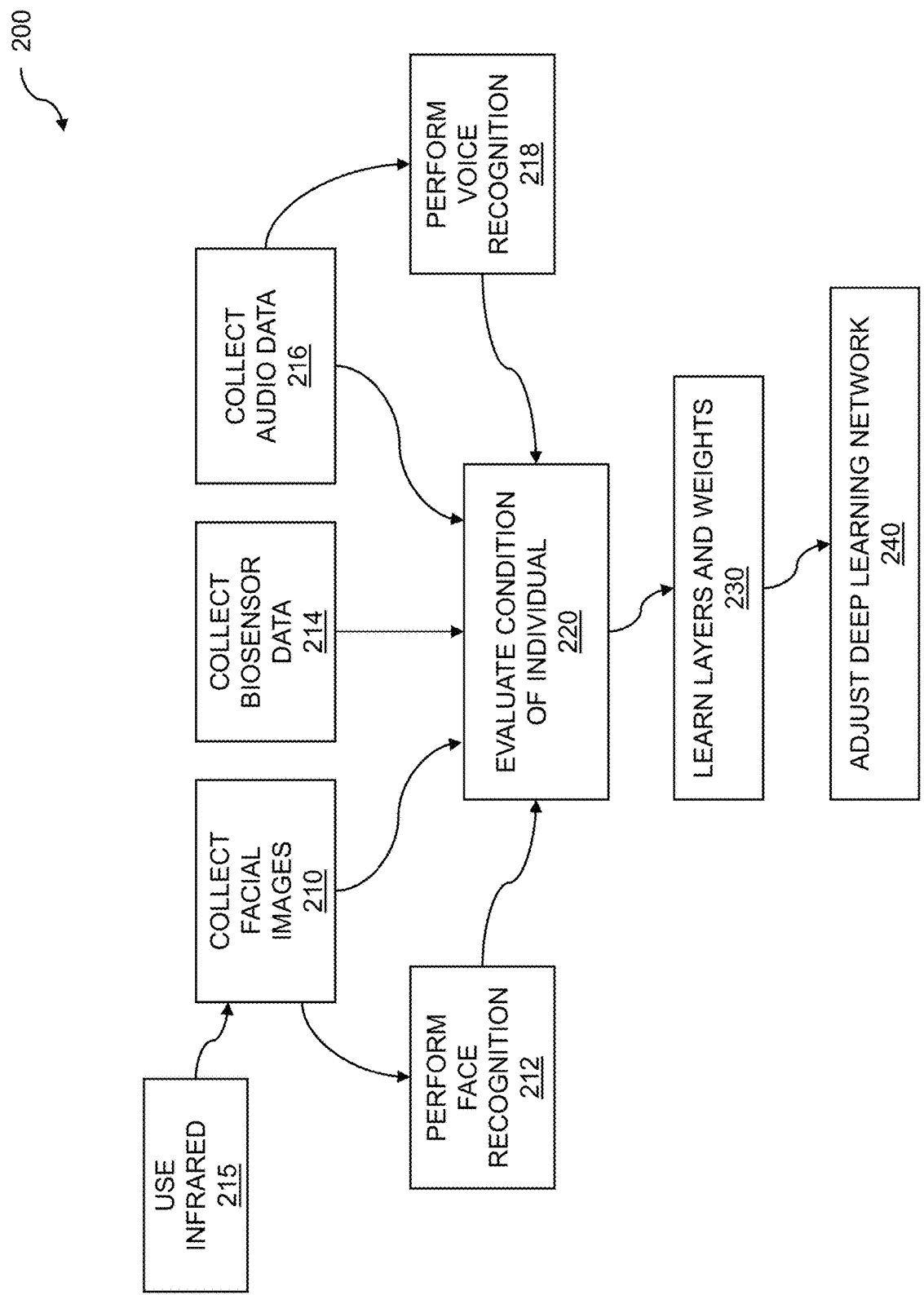
FIG. 2 is a flow diagram for adjusting deep learning for evaluating an individual.

FIG. 2 is a flow diagram for adjusting deep learning for evaluating an individual. Deep learning techniques can be applied to cognitive analysis and can be used for directed control transfer for autonomous vehicles. In-vehicle sensors are used to collect cognitive state data for an individual within a vehicle which has an autonomous mode of operation. One or more processors, whether in-vehicle or extra-vehicle, are used to analyze the cognitive state data collected from the individual to produce cognitive state information. The individual is scored based on the cognitive state information to produce a cognitive scoring metric. A state of operation for the vehicle can include manual operation, semi-autonomous operation, or autonomous operation. A condition of the individual is evaluated based on the cognitive scoring metric. Control is transferred between the vehicle and the individual based on the state of operation of the vehicle and the condition of the individual.

The flow 200 includes collecting facial images 210 from the individual. In embodiments, the cognitive state data can include the facial image data from the individual. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The camera can be coupled to an autonomous vehicle. Image data based on wavelengths of light other than visible light can be captured using in-vehicle imaging devices, in-vehicle biosensor devices, and so on. In embodiments, the using in-vehicle sensors includes using one or more infrared imaging sensors 215. The flow 200 further includes performing facial recognition 212 on the individual. The facial recognition can be used to set up an autonomous vehicle based on the preferences of an individual such as preferred music, vehicle cabin climatic conditions, seat positions, etc. The flow 200 includes collecting cognitive state data that includes biosensor data 214 from the individual. The biosensor data can be used to determine a cognitive state of the individual, a condition of the individual, etc. In embodiments, the biosensor data can include heart rate, heart rate variability, electrodermal activity, acceleration, or the like.

The flow 200 includes collecting cognitive state data which includes audio data 216 from the individual. The audio data can include acoustic signals that can be collected using one or more microphones within the autonomous vehicle. The audio data can include a variety of acoustic signals. In embodiments, the audio data includes voice data from the individual. The voice data can include language verbiage. In embodiments, the voice data can include spoken language information. Other acoustic signals including audio data can be collected. In embodiments, the voice data can include non-speech vocalizations. The non-speech vocalizations can include a variety of sounds that can be generated by the individual. In embodiments, the non-speech vocalizations can include grunts, yelps, squeals, snoring, sighs, laughter, filled pauses, unfilled pauses, or yawns. The flow 200 further includes performing voice recognition 218 on the individual. The performing voice recognition can be used to configure the autonomous vehicle based on voice commands from the individual. The voice recognition can be used to issue commands, instructions, requests, etc., to the autonomous vehicle.

The flow 200 includes evaluating a condition of the individual 220 based on a cognitive scoring metric. The individual can be evaluated for a variety of purposes, where the purposes can include determining whether the individual is permitted to control a given vehicle, whether the individual is physically or cognitively capable of operating the vehicle, and so on. In embodiments, the condition of the individual can include being alert, engaged, impaired, asleep, unconscious, reclined, drowsy, fatigued, inattentive; exhibiting antisocial behavior; or the like. The cognitive scoring metric can be used as a basis for making a variety of decisions such as "go or no-go" decisions, "yes or no" decisions, etc. In embodiments, the cognitive scoring metric includes a numeric representation for a mental state. The mental state can be used to infer whether a driver may control the vehicle. The cognitive scoring metric, which can be based on scoring the individual, can be used in detection of one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. The numeric representation of the mental state can be based on one or more action units (AU), intensities, and so on. The numeric representation can include a probability for occurrence of the mental state, an intensity range, etc.

The evaluating the condition of the individual can be based on machine learning. In the flow 200, the machine learning includes learning layers and weights 230 for a deep learning network. One or more layers can be included in a network that can be used for deep learning. As discussed below, the layers can include an input layer, convolution layers, pooling layers, rectified linear units (ReLU), fully connected layers, an output layer, and so on. The numbers of layers that can be used can be based on machine learning techniques. The weights that can be learned can be used to speed convergence, to improve accuracy of classifications, to improve detection of faces and voices, and so on. In embodiments, the deep learning network includes a convolutional neural network. The deep learning network can include a deep neural network.

The flow 200 includes adjusting the deep learning network 240. Many techniques can be applied to adjusting the deep learning network. The adjustments can be used to improve accuracy for such tasks as facial recognition 212, voice recognition 218, and so on. Other adjustments can include starting points for learning, information related to the individual, and so on. In embodiments the machine learning can be tailored for the individual. The tailoring to the individual can be based on user information for the individual. In embodiments, the machine learning and the tailoring can be based on a profile for the individual. The tailoring can be based on a user ID, login credentials, biometric data, and the like. In other embodiments, the machine learning can be initiated based on a demographic for the individual. A demographic can include one or more of age, gender identity, cultural identity, racial identity, geographic location, and the like. A set of layers and weights, such as those discussed above, can be used as an initial point based on the demographic for the individual. The adjusting the deep learning network can rely on cognitive state data that is collected from and analyzed for a plurality of people. The adjusting can be based on collaboration. In embodiments, the set of layers and weights is further developed through collaborative filtering. The deep learning network and the adjusting the deep learning network can be based on historical data for the individual. The historical data can include travel route preferences, time of day for travel, business travel or leisure travel, vehicle cabin climatic conditions, etc. The deep learning network can be adjusted according to the individual operating a second vehicle. Further embodiments can include sharing results of the machine learning with a second vehicle. The sharing the results of the machine learning can be particularly useful when the second vehicle is a similar vehicle, such as a second vehicle from a fleet of vehicles. The second vehicle need not be identical to the first vehicle. The second vehicle can be different from the first vehicle. Data can be collected from the vehicles with which the results of the machine learning can be shared. In further embodiments, the sharing results can include distributed model training. Various steps in the flow 200 may be changed in order, repeated, omitted, or the like without departing from the disclosed concepts. Various embodiments of the flow 200 can be included in a computer program product embodied in a non-transitory computer readable medium that includes code executable by one or more processors.

Figure 3:
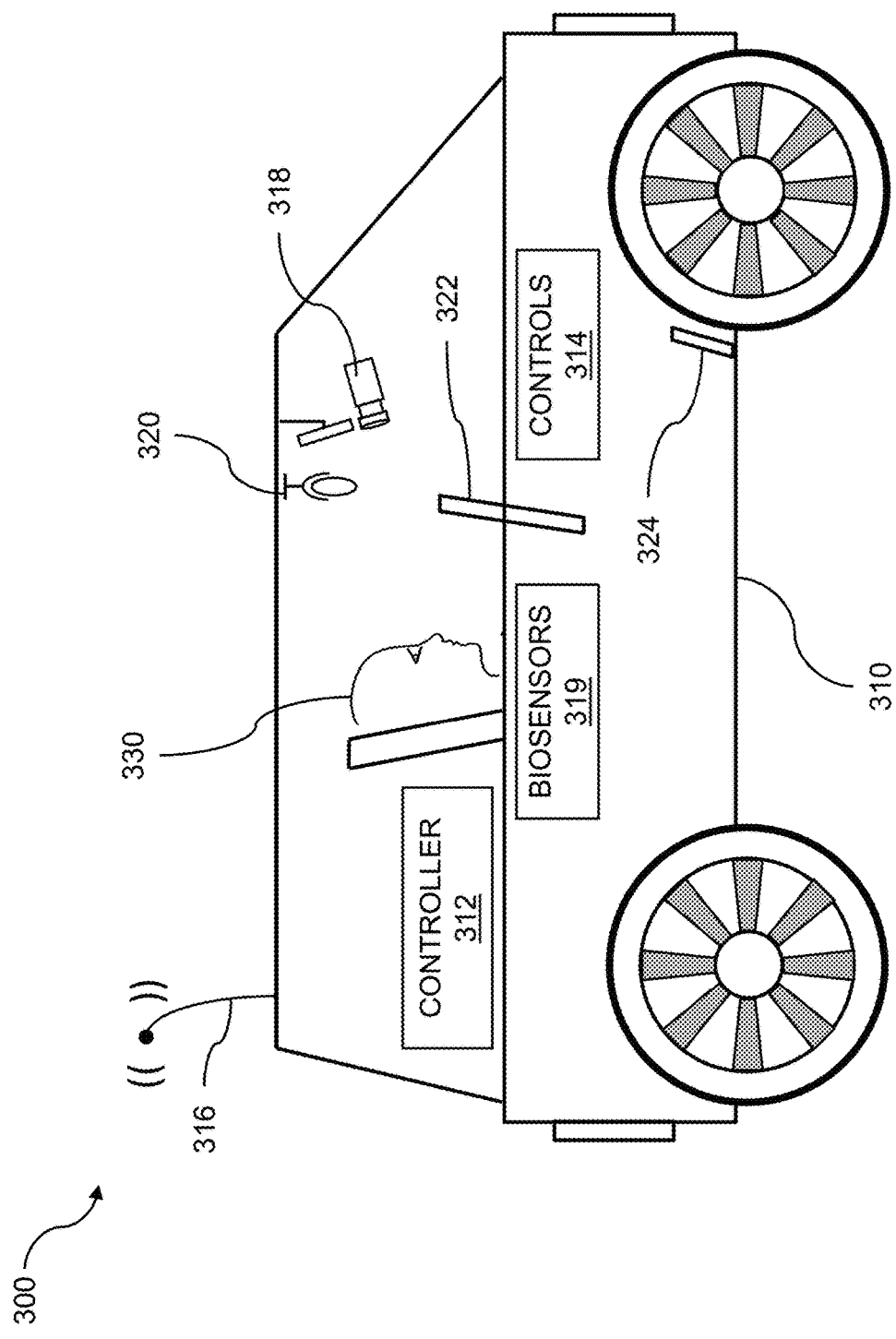
FIG. 3 is a system diagram for a vehicle interior showing controls.

FIG. 3 is a system diagram for a vehicle interior 300 showing controls. Vehicle manipulation can be based on vehicle occupant cognitive analysis. The cognitive analysis can be used for directed control transfer for autonomous vehicles. In-vehicle sensors are used for collecting cognitive state data for an individual within a vehicle. The vehicle can have an autonomous mode of operation, a semi-autonomous mode of operation, and a manual mode of operation. Processors are used to analyze the cognitive state data collected from the individual to produce cognitive state information. The processors can include processors within the vehicle, processors remotely located from the vehicle, and the like. The individual is scored based on the cognitive state information to produce a cognitive scoring metric. The scoring metric can include permission to operate the vehicle, an ability ranking to operate the vehicle, a level of impairment, and so on. A state of operation is determined for the vehicle. The state of operation can include manual mode, semi-autonomous mode, or autonomous mode. A condition of the individual is evaluated based on the cognitive scoring metric. The condition of the individual can include being alert, engaged, impaired, asleep, unconscious, reclined, drowsy, fatigued, inattentive, or exhibiting antisocial behavior, etc. Control is transferred between the vehicle and the individual based on the state of operation of the vehicle and the condition of the individual. The transfer of control of the vehicle can include transferring control from a vehicle in autonomous mode to the individual who can operate the vehicle in manual mode or semi-autonomous mode. The transfer of control of the vehicle can include transferring control from the individual to the vehicle in autonomous mode.

An occupant 330 of a vehicle 310 can be observed by using a camera 318, a microphone 320, and other image and audio capture techniques. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The occupant of the individual can be observed or monitored using one or more biosensors 319. The biosensors can be used to collect biosensor data, where the biosensor data can include heart rate, heart rate variability, electrodermal activity, or acceleration. Other in-vehicle sensors can be used to collect biological data, image data, audio data, and so on. In embodiments, the in-vehicle sensors can include one or more infrared imaging sensors. The image data can include video data, facial data, etc. The video data and the audio data can include cognitive state data. The occupant can be a driver of the vehicle 310, a passenger within the vehicle, and so on. The interior of a vehicle 310 can be the interior of a standard vehicle, an autonomous vehicle, a semi-autonomous vehicle, and so on. The vehicle can be an automobile, a van, a sport utility vehicle (SUV), a truck, a bus, a special purpose vehicle, etc. The interior of the vehicle 310 can include standard controls such as a steering wheel 322, a throttle control (not shown), a brake 324, and so on. The interior of the vehicle can include other controls 314 such as controls for seats, mirrors, climate adjustment, entertainment center selections, etc. The controls 314 of the vehicle 310 can be controlled by a controller 312. The controller 312 can control the vehicle 310 in various manners such as autonomously, semi-autonomously, assertively to a vehicle occupant 330, etc. In embodiments, the controller provides vehicle control techniques, assistance, etc. The controller 312 can receive instructions via an antenna 316 or using other wireless techniques. The controller 312 can be preprogrammed to cause the vehicle to follow a specific route.

Figure 4:
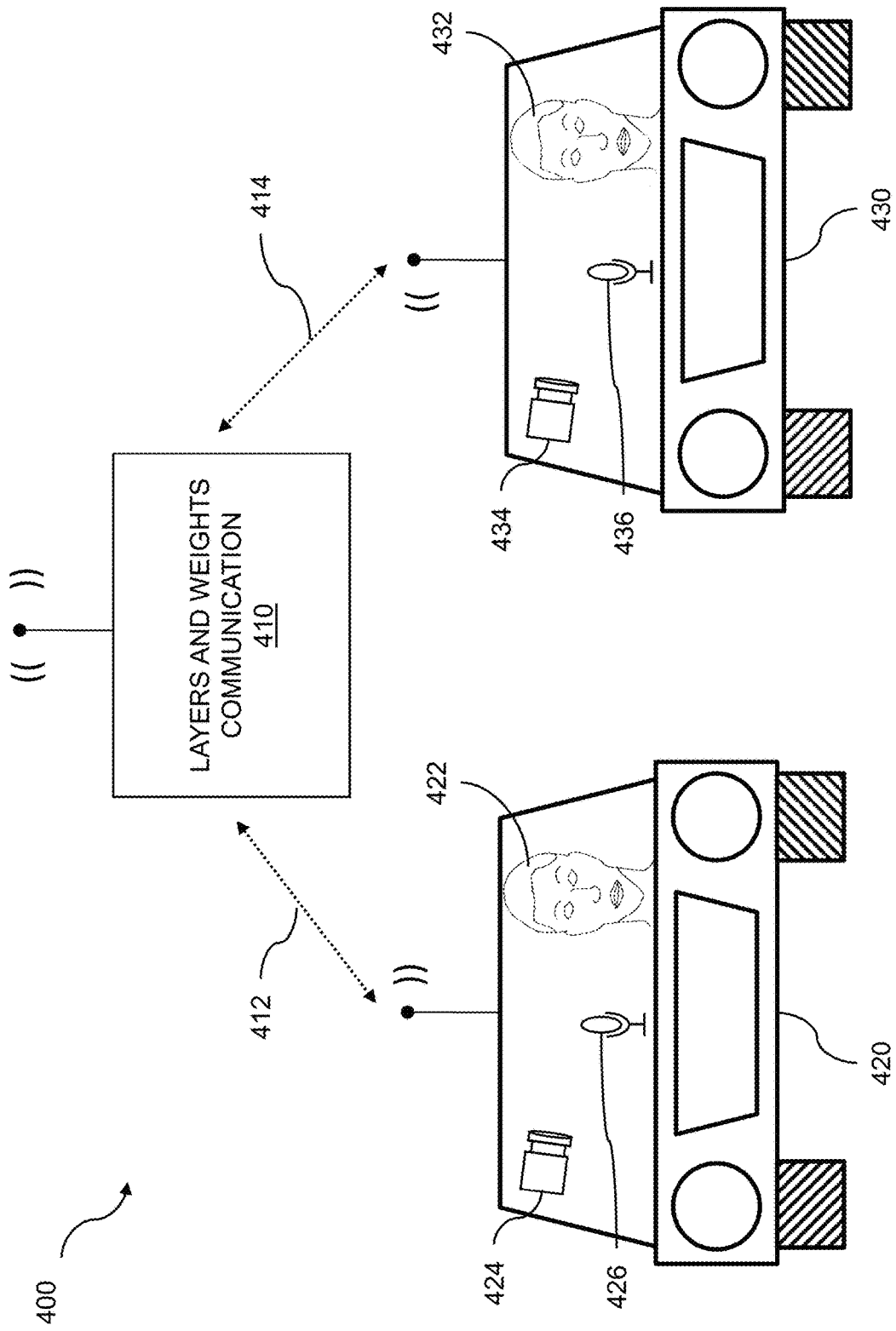
FIG. 4 is a system diagram for vehicle artificial intelligence evaluation.

FIG. 4 is a system diagram for vehicle artificial intelligence evaluation. Cameras, microphones, and other sensors such as infrared sensors can be used for collecting cognitive state data from a general population. The cognitive state data can include facial data, voice data, physiological data, infrared imaging data, and so on. The cognitive state data that is collected is used for learning layers and weights of a deep neural network. The layers and weights of the deep neural network can be used for directed control transfer for autonomous vehicles, where the directed control transfer can be between the vehicle and an individual. The transfer of control can be based on both the state of operation of the vehicle, such as autonomous operation, manual operation, etc., and a condition of the individual. The condition of the individual can include being alert, engaged, impaired, asleep, unconscious, reclined, drowsy, fatigued, inattentive, or exhibiting antisocial behavior. A system diagram for vehicle artificial intelligence evaluation of cognitive analysis 400 is shown. The system can include cognitive state data, cognitive state information, and layers and weights communication 410. The communicating cognitive state data can include cognitive state data, including image data and audio data, that can be collected from an individual. The communicating of the layers and weights can include sending adjusted levels and adjusted weights to a first vehicle 420, to a second vehicle 430, and so on.

The layers and weights can be sent to a first vehicle 420 using a network such as a wireless link 412 or other data transfer technique. The cognitive state data and cognitive state information can be sent over the same wireless link 412 or a different wireless link. The layers and weights that can be sent can be based on cognitive state data including facial data from an occupant 422 of the vehicle 420. The cognitive state data including facial data can be collected using a camera 424 or other image capture technique. The cognitive state data can include in-vehicle sensor data. In embodiments, the in-vehicle sensor data can include data collected using one or more infrared imaging sensors. The system 400 can include collecting voice data and augmenting the cognitive state data with the voice data. The voice data can be collected from the occupant 422 using a microphone 426 or other audio capture technique. The voice data can include audio data, where the audio data can include traffic sounds, road noise, music that can be played by the occupant, and so on. The system 400 can include evaluating the voice data for timbre, prosody, vocal register, vocal resonance, pitch, loudness, speech rate, or language content. The evaluating the voice data can also be used in evaluating the cognitive state or states of the occupant 422 of the vehicle 420. In embodiments, the augmenting can be based on lexical analysis of the voice data that looks at sentiment. As for the first vehicle, the cognitive state profile can be sent to a second vehicle 430 using a wireless link 414 or other data transfer technique. The cognitive state profile can be based on cognitive state data including facial data from an occupant 432 of the vehicle 430, can be based on the cognitive state data including facial data from the occupant 422 of the first vehicle 420, and so on. The cognitive state data including facial data can be collected using a camera 434 or other image capture technique. The system 400 can include collecting voice data from the occupant 432 using a microphone 436 or other audio capture technique.

Figure 5:
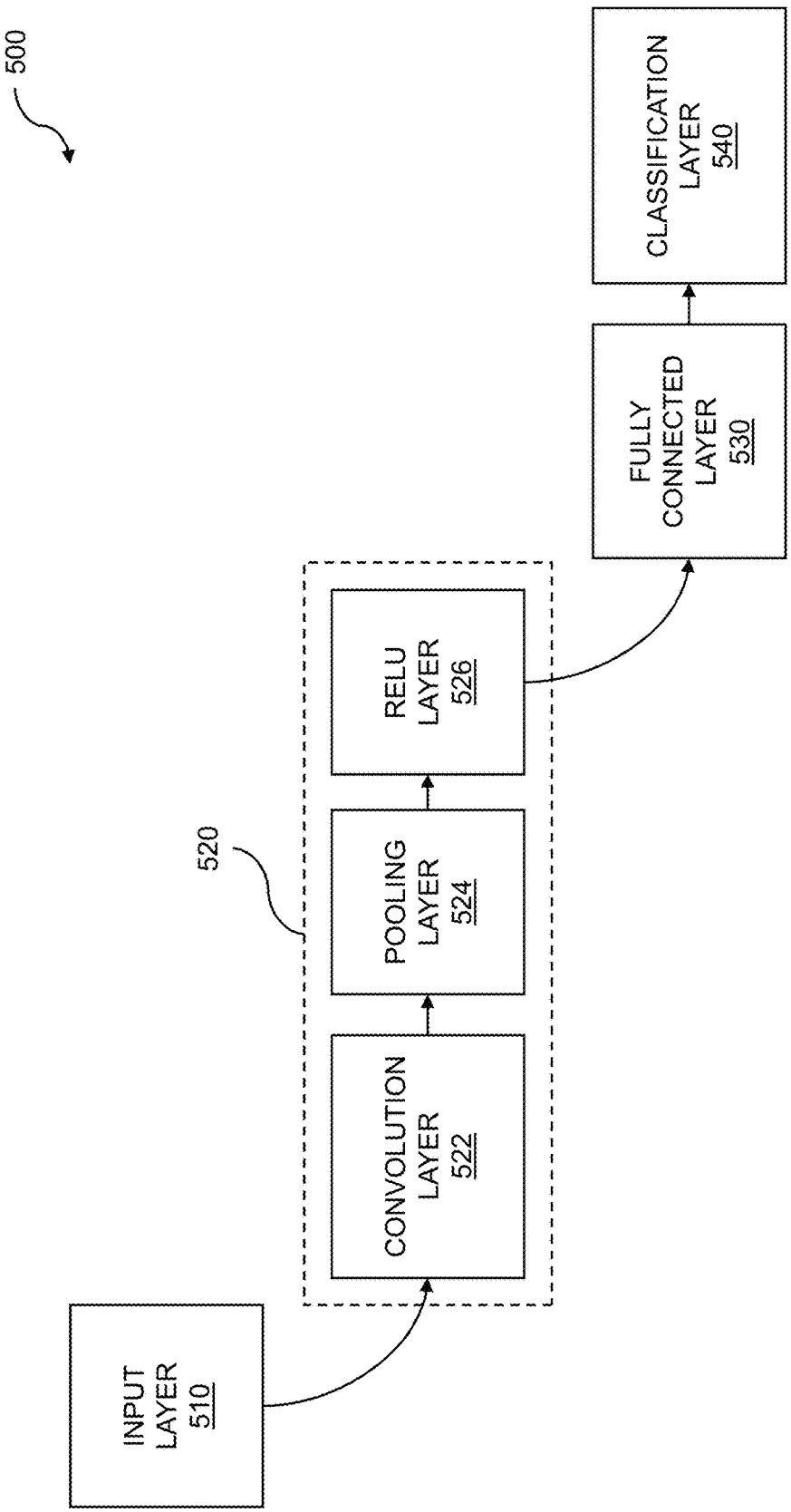
FIG. 5 is an example showing a convolutional neural network.

FIG. 5 is an example showing a convolutional neural network (CNN). The convolutional neural network can be used for deep learning, where the deep learning can be applied to directed control transfer for autonomous vehicles. The directed control transfer can be based on a state of operation for the vehicle and a condition of an individual. The convolutional neural network can be applied to such tasks as cognitive state analysis, mental state analysis, mood analysis, emotional state analysis, and so on. The various analyses can be applied to video data, audio data, or sensor data, where the sensor data can include infrared imagining data. Cognitive state data can include mental processes, where the mental processes can include attention, creativity, memory, perception, problem solving, thinking, use of language, or the like.

Emotion analysis is a considerably complex task. Understanding and evaluating moods, emotions, mental states, or cognitive states requires a nuanced evaluation of facial expressions and other cues generated by people. Cognitive state analysis is important in many areas such as research, psychology, business, intelligence, law enforcement, and so on. The understanding of cognitive states can be useful for a variety of business purposes, such as improving marketing analysis, assessing the effectiveness of customer service interactions and retail experiences, and evaluating the consumption of content such as movies and videos. Identifying points of frustration in a customer transaction can allow a company to take action to address the causes of the frustration. By streamlining processes, key performance areas such as customer satisfaction and customer transaction throughput can be improved, resulting in increased sales and revenues. In a content scenario, producing compelling content that achieves the desired effect (e.g. fear, shock, laughter, etc.) can result in increased ticket sales and/or increased advertising revenue. If a movie studio is producing a horror movie, it is desirable to know if the scary scenes in the movie are achieving the desired effect. By conducting tests in sample audiences and analyzing faces in the audience, a computer-implemented method and system can process thousands of faces to assess the cognitive state at the time of the scary scenes. In many ways, such an analysis can be more effective than surveys that ask audience members questions, since audience members may consciously or subconsciously change answers based on peer pressure or other factors. However, spontaneous facial expressions can be more difficult to conceal. Thus, by analyzing facial expressions en masse in real time, important information regarding the general cognitive state of the audience can be obtained.

Analysis of facial expressions is also a complex task. Image data, where the image data can include facial data, can be analyzed to identify a range of facial expressions. The facial expressions can include a smile, frown, smirk, and so on. The image data and facial data can be processed to identify the facial expressions. The processing can include analysis of expression data, action units, gestures, mental states, cognitive states, physiological data, and so on. Facial data as contained in the raw video data can include information on one or more of action units, head gestures, smiles, brow furrows, squints, lowered eyebrows, raised eyebrows, attention, and the like. The action units can be used to identify smiles, frowns, and other facial indicators of expressions. Gestures can also be identified, and can include a head tilt to the side, a forward lean, a smile, a frown, as well as many other gestures. Other types of data including the physiological data can be collected, where the physiological data can be obtained using a camera or other image capture device, without contacting the person or persons. Respiration, heart rate, heart rate variability, perspiration, temperature, and other physiological indicators of cognitive state can be determined by analyzing the images and video data.

Deep learning is a branch of machine learning which seeks to imitate in software the activity which takes place in layers of neurons in the neocortex of the human brain. This imitative activity can enable software to "learn" to recognize and identify patterns in data, where the data can include digital forms of images, sounds, and so on. The deep learning software is used to simulate the large array of neurons of the neocortex. This simulated neocortex, or artificial neural network, can be implemented using mathematical formulas that are evaluated on processors. With the ever-increasing capabilities of the processors, increasing numbers of layers of the artificial neural network can be processed.

Deep learning applications include processing of image data, audio data, and so on. Image data applications include image recognition, facial recognition, etc. Image data applications can include differentiating dogs from cats, identifying different human faces, and the like. The image data applications can include identifying cognitive states, moods, mental states, emotional states, and so on, from the facial expressions of the faces that are identified. Audio data applications can include analyzing audio such as ambient room sounds, physiological sounds such as breathing or coughing, noises made by an individual such as tapping and drumming, voices, and so on. The voice data applications can include analyzing a voice for timbre, prosody, vocal register, vocal resonance, pitch, loudness, speech rate, or language content. The voice data analysis can be used to determine one or more cognitive states, moods, mental states, emotional states, etc.

The artificial neural network, such as a convolutional neural network which forms the basis for deep learning, is based on layers. The layers can include an input layer, a convolution layer, a fully connected layer, a classification layer, and so on. The input layer can receive input data such as image data, where the image data can include a variety of formats including pixel formats. The input layer can then perform processing such as identifying boundaries of the face, identifying landmarks of the face, extracting features of the face, and/or rotating a face within the plurality of images. The convolution layer can represent an artificial neural network such as a convolutional neural network. A convolutional neural network can contain a plurality of hidden layers within it. A convolutional layer can reduce the amount of data feeding into a fully connected layer. The fully connected layer processes each pixel/data point from the convolutional layer. A last layer within the multiple layers can provide output indicative of cognitive state. The last layer of the convolutional neural network can be the final classification layer. The output of the final classification layer can be indicative of the cognitive states of faces within the images that are provided to the input layer.

Deep networks including deep convolutional neural networks can be used for facial expression parsing. A first layer of the deep network includes multiple nodes, where each node represents a neuron within a neural network. The first layer can receive data from an input layer. The output of the first layer can feed to a second layer, where the latter layer also includes multiple nodes. A weight can be used to adjust the output of the first layer which is being input to the second layer. Some layers in the convolutional neural network can be hidden layers. The output of the second layer can feed to a third layer. The third layer can also include multiple nodes. A weight can adjust the output of the second layer which is being input to the third layer. The third layer may be a hidden layer. Outputs of a given layer can be fed to next layer. Weights adjust the output of one layer as it is fed to the next layer. When the final layer is reached, the output of the final layer can be a facial expression, a cognitive state, a mental state, a characteristic of a voice, and so on. The facial expression can be identified using a hidden layer from the one or more hidden layers. The weights can be provided on inputs to the multiple layers to emphasize certain facial features within the face. The convolutional neural network can be trained to identify facial expressions, voice characteristics, etc. The training can include assigning weights to inputs on one or more layers within the multilayered analysis machine. One or more of the weights can be adjusted or updated during training. The assigning weights can be accomplished during a feed-forward pass through the multilayered neural network. In a feed-forward arrangement, the information moves forward from the input nodes, through the hidden nodes, and on to the output nodes. Additionally, the weights can be updated during a backpropagation process through the multilayered analysis machine.

Returning to the figure, FIG. 5 is an example showing a convolutional neural network 500. The convolutional neural network can be used for deep learning, where the deep learning can be applied to avatar image animation using translation vectors. The deep learning system can be accomplished using a convolution neural network or other techniques. The deep learning can accomplish facial recognition and analysis tasks. The network includes an input layer 510. The input layer 510 receives image data. The image data can be input in a variety of formats, such as JPEG, TIFF, BMP, and GIF. Compressed image formats can be decompressed into arrays of pixels, wherein each pixel can include an RGB tuple. The input layer 510 can then perform processing such as identifying boundaries of the face, identifying landmarks of the face, extracting features of the face, and/or rotating a face within the plurality of images.

The network includes a collection of intermediate layers 520. The multilayered analysis machine can include a convolutional neural network. Thus, the intermediate layers can include a convolution layer 522. The convolution layer 522 can include multiple sublayers, including hidden layers within it. The output of the convolution layer 522 feeds into a pooling layer 524. The pooling layer 524 performs a data reduction, which makes the overall computation more efficient. Thus, the pooling layer reduces the spatial size of the image representation to reduce the number of parameters and computation in the network. In some embodiments, the pooling layer is implemented using filters of size 2×2, applied with a stride of two samples for every depth slice along both width and height, resulting in a reduction of 75-percent of the downstream node activations. The multilayered analysis machine can further include a max pooling layer 524. Thus, in embodiments, the pooling layer is a max pooling layer, in which the output of the filters is based on a maximum of the inputs. For example, with a 2×2 filter, the output is based on a maximum value from the four input values. In other embodiments, the pooling layer is an average pooling layer or L2-norm pooling layer. Various other pooling schemes are possible.

The intermediate layers can include a Rectified Linear Units (RELU) layer 526. The output of the pooling layer 524 can be input to the RELU layer 526. In embodiments, the RELU layer implements an activation function such as $f(x)=\max(0,x)$, thus providing an activation with a threshold at zero. In some embodiments, the RELU layer 526 is a leaky RELU layer. In this case, instead of the activation function providing zero when x<0, a small negative slope is used, resulting in an activation function such as $f(x)=1(x<0)(\alpha x)+1(x>=0)(x)$. This can reduce the risk of "dying RELU" syndrome, where portions of the network can be "dead" with nodes/neurons that do not activate across the training dataset. The image analysis can comprise training a multilayered analysis machine using the plurality of images, wherein the multilayered analysis machine can comprise multiple layers that include one or more convolutional layers 522 and one or more hidden layers, and wherein the multilayered analysis machine can be used for emotional analysis.

The example 500 includes a fully connected layer 530. The fully connected layer 530 processes each pixel/data point from the output of the collection of intermediate layers 520. The fully connected layer 530 takes all neurons in the previous layer and connects them to every single neuron it has. The output of the fully connected layer 530 provides input to a classification layer 540. The output of the classification layer 540 provides a facial expression and/or cognitive state as its output. Thus, a multilayered analysis machine such as the one depicted in FIG. 5 processes image data using weights, models the way the human visual cortex performs object recognition and learning, and is effective for analysis of image data to infer facial expressions and cognitive states.

Machine learning for generating parameters, analyzing data such as facial data and audio data, and so on, can be based on a variety of computational techniques. Generally, machine learning can be used for constructing algorithms and models. The constructed algorithms, when executed, can be used to make a range of predictions relating to data. The predictions can include whether an object in an image is a face, a box, or a puppy; whether a voice is female, male, or robotic; whether a message is legitimate email or a "spam" message; and so on. The data can include unstructured data and can be of large quantity. The algorithms that can be generated by machine learning techniques are particularly useful to data analysis because the instructions that comprise the data analysis technique do not need to be static. Instead, the machine learning algorithm or model, generated by the machine learning technique, can adapt. Adaptation of the learning algorithm can be based on a range of criteria such as success rate, failure rate, and so on. A successful algorithm is one that can adapt—or learn—as more data is presented to the algorithm. Initially, an algorithm can be "trained" by presenting it with a set of known data (supervised learning). Another approach, called unsupervised learning, can be used to identify trends and patterns within data. Unsupervised learning is not trained using known data prior to data analysis.

Reinforced learning is an approach to machine learning that is inspired by behaviorist psychology. The underlying premise of reinforced learning (also called reinforcement learning) is that software agents can take actions in an environment. The actions that are taken by the agents should maximize a goal such as a "cumulative reward". A software agent is a computer program that acts on behalf of a user or other program. The software agent is implied to have the authority to act on behalf of the user or program. The actions taken are decided by action selection to determine what to do next. In machine learning, the environment in which the agents act can be formulated as a Markov decision process (MDP). The MDPs provide a mathematical framework for modeling of decision making in environments where the outcomes can be partly random (stochastic) and partly under the control of the decision maker. Dynamic programming techniques can be used for reinforced learning algorithms. Reinforced learning is different from supervised learning in that correct input/output pairs are not presented, and suboptimal actions are not explicitly corrected. Rather, on-line or computational performance is the focus. On-line performance includes finding a balance between exploration of new (uncharted) territory or spaces, and exploitation of current knowledge. That is, there is a tradeoff between exploration and exploitation.

Machine learning based on reinforced learning adjusts or learns based on learning an action, a combination of actions, and so on. An outcome results from taking an action. Thus, the learning model, algorithm, etc., learns from the outcomes that result from taking the action or combination of actions. The reinforced learning can include identifying positive outcomes, where the positive outcomes are used to adjust the learning models, algorithms, and so on. A positive outcome can be dependent on a context. When the outcome is based on a mood, emotional state, mental state, cognitive state, etc., of an individual, then a positive mood, emotion, mental state, or cognitive state can be used to adjust the model and algorithm. Positive outcomes can include a person being more engaged, where engagement is based on affect, the person spending more time playing an online game or navigating a webpage, the person converting by buying a product or service, and so on. The reinforced learning can be based on exploring a solution space and adapting the model, algorithm, etc., based on outcomes of the exploration. When positive outcomes are encountered, the positive outcomes can be reinforced by changing weighting values within the model, algorithm, etc. Positive outcomes may result in increasing weighting values. Negative outcomes can also be considered, where weighting values may be reduced or otherwise adjusted.

Figure 6:
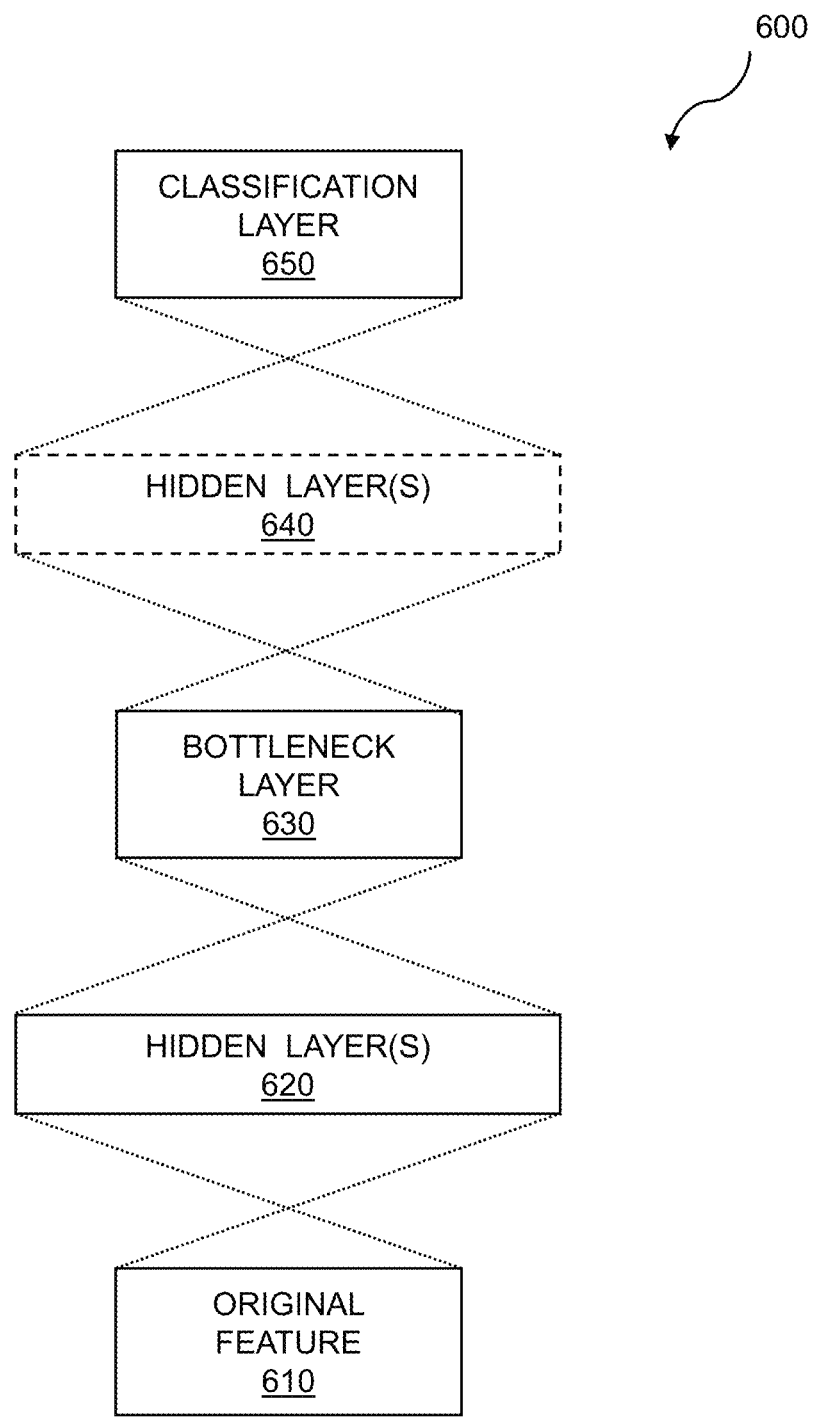
FIG. 6 illustrates a bottleneck layer within a deep learning environment.

FIG. 6 illustrates a bottleneck layer within a deep learning environment. A bottleneck layer can be a layer of a plurality of layers within a deep neural network. The bottleneck layer within the deep neural network can be used for directed control transfer for autonomous vehicles. The deep learning environment can be used to learn about analysis of video data, audio data, sensor data, and so on. The sensor data can include infrared sensor data. Control can be transferred between the vehicle and an individual. The transfer of control can be based on the state of operation of the vehicle, where the state of operation of the vehicle can include autonomous operation, manual operation, and so on. The transfer of control can also be based on the condition of the individual, where the condition of the individual can include being alert, engaged, impaired, asleep, unconscious, reclined, drowsy, fatigued, or inattentive; exhibiting antisocial behavior; or the like.

Layers of a deep neural network 600 can include a bottleneck layer. A bottleneck layer can be used for a variety of applications such as facial recognition, voice recognition, emotional state recognition, and so on. The deep neural network in which the bottleneck layer is located can include a plurality of layers. The plurality of layers can include an original feature layer 610. A feature such as an image feature can include points, edges, objects, boundaries between and among regions, properties, and so on. The deep neural network can include one or more hidden layers 620. The one or more hidden layers can include nodes, where the nodes can include nonlinear activation functions and other techniques. The bottleneck layer can be a layer that learns translation vectors to transform a neutral face to an emotional or expressive face. In some embodiments, the translation vectors can transform a neutral sounding voice to an emotional or expressive voice. Specifically, activations of the bottleneck layer determine how the transformation occurs. A single bottleneck layer can be trained to transform a neutral face or voice to an emotionally expressive face or voice. In some cases, individual bottleneck layers can be trained for a transformation pair. At runtime, once the user's emotion has been identified and an appropriate response to it can be determined (mirrored or complementary), the trained bottleneck layer can be used to perform the needed transformation.

The deep neural network can include a bottleneck layer 630. The bottleneck layer can include a fewer number of nodes than the one or more preceding hidden layers. The bottleneck layer can create a constriction in the deep neural network or other network. The bottleneck layer can force information that is pertinent to a classification, for example, into a low dimensional representation. The bottleneck features can be extracted using an unsupervised technique. In other embodiments, the bottleneck features can be extracted in a supervised manner. The supervised technique can include training the deep neural network with a known dataset. The features can be extracted from an autoencoder such as a variational autoencoder, a generative autoencoder, and so on. The deep neural network can include hidden layers 640. The number of hidden layers can include zero hidden layers, one hidden layer, a plurality of hidden layers, and so on. The hidden layers following the bottleneck layer can include more nodes than the bottleneck layer. The deep neural network can include a classification layer 650. The classification layer can be used to identify the points, edges, objects, boundaries, and so on, described above. The classification layer can be used to identify cognitive states, mental states, emotional states, moods, and the like. The output of the final classification layer can be indicative of the emotional states of faces within the images, where the images can be processed using the deep neural network.

Figure 7:
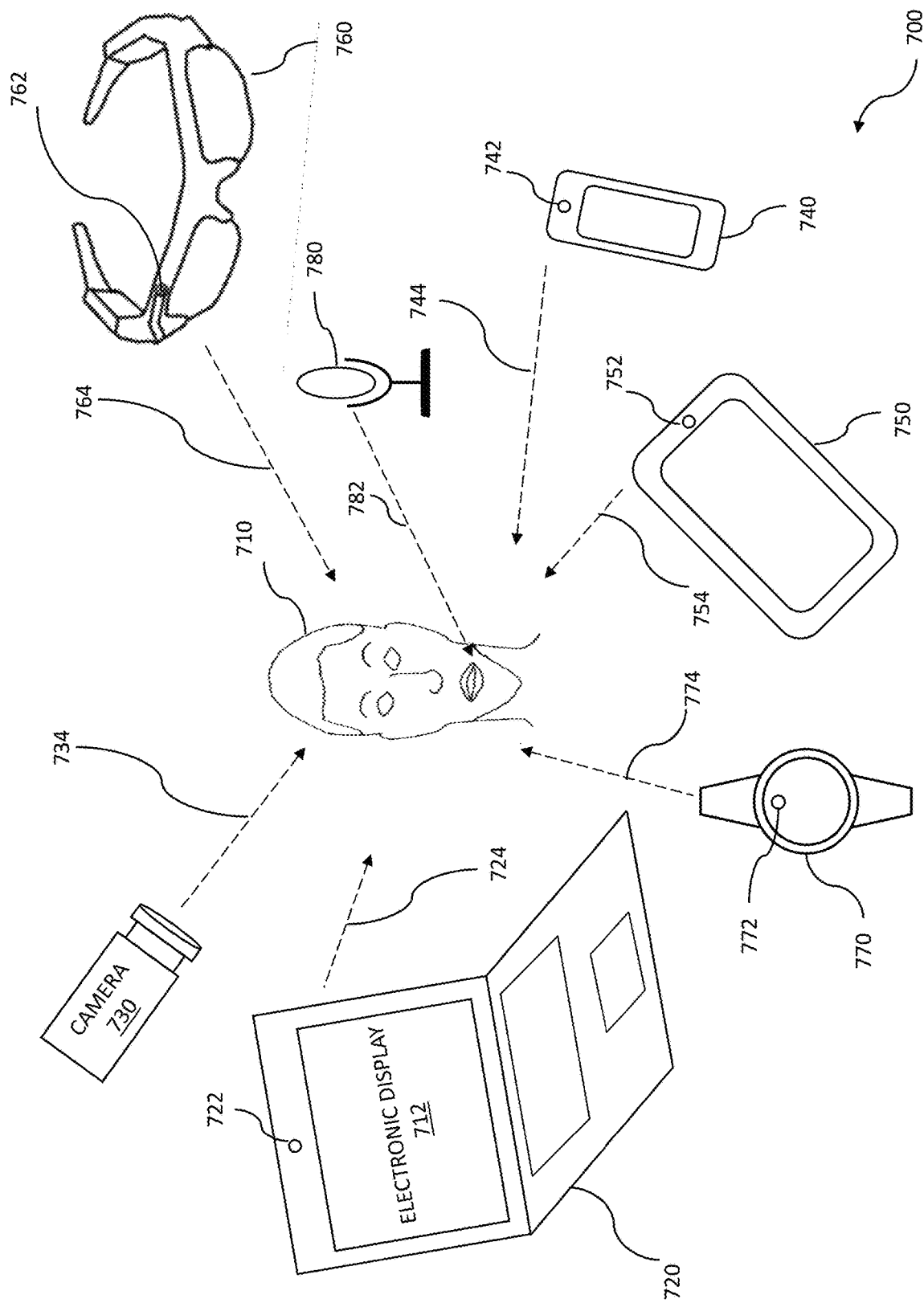
FIG. 7 is a diagram showing image and audio collection including multiple mobile devices.

FIG. 7 is a diagram showing image and audio collection including multiple mobile devices. Data including image data and audio data can be collected using multiple mobile devices, where the data can be used for directed control transfer for autonomous vehicles. Control can be transferred between the autonomous vehicle and an individual based on both the state of operation of the vehicle, such as autonomous operation or manual operation, and a condition of the individual. In the diagram 700, the multiple mobile devices can be used separately or in combination to collect video data, audio data, or both video data and audio data on a user 710. In embodiments, the multiple mobile devices can be used to collect sensor data, where the sensor data can include infrared sensor data. While one person is shown, the video data and audio data can be collected on multiple people. A user 710 can be observed as she or he is performing a task, experiencing an event, viewing a media presentation, and so on. The user 710 can be shown one or more media presentations, political presentations, social media, or another form of displayed media. The one or more media presentations can be shown to a plurality of people. The media presentations can be displayed on an electronic display 712 or another display. The data collected on the user 710 or on a plurality of users can be in the form of one or more videos, video frames, still images, one or more audio channels, etc. The plurality of video data and audio data can be of people who are experiencing different situations. Some example situations can include the user or plurality of users being exposed to TV programs, movies, video clips, social media, and other such media. The situations could also include exposure to media such as advertisements, political messages, news programs, and so on.

As noted before, video data and audio data can be collected on one or more users in substantially identical or different situations and viewing either a single media presentation or a plurality of presentations. The data collected on the user 710 can be analyzed and viewed for a variety of purposes including expression analysis, cognitive state analysis, mental state analysis, emotional state analysis, and so on. The electronic display 712 can be on a laptop computer 720 as shown, a tablet computer 750, a cell phone 740, a television, a mobile monitor, or any other type of electronic device. In one embodiment, video data including expression data is collected on a mobile device such as a cell phone 740, a tablet computer 750, a laptop computer 720, or a watch 770. Similarly, the audio data including speech data and non-speech vocalizations can be collected on one or more of the mobile devices. Thus, the multiple sources can include at least one mobile device, such as a phone 740 or a tablet 750, or a wearable device such as a watch 770 or glasses 760. A mobile device can include a forward-facing camera and/or a rear-facing camera that can be used to collect expression data. A mobile device can include a microphone, audio transducer, or other audio capture apparatus that can be used to capture the speech and non-speech vocalizations. Sources of expression data can include a webcam 722, a phone camera 742, a tablet camera 752, a wearable camera 762, and a mobile camera 730. A wearable camera can comprise various camera devices, such as a watch camera 772. Sources of audio data 782 can include a microphone 780.

As the user 710 is monitored, the user 710 might move due to the nature of the task, boredom, discomfort, distractions, or for another reason. As the user moves, the camera with a view of the user's face can be changed. Thus, as an example, if the user 710 is looking in a first direction, the line of sight 724 from the webcam 722 is able to observe the user's face, but if the user is looking in a second direction, the line of sight 734 from the mobile camera 730 is able to observe the user's face. Furthermore, in other embodiments, if the user is looking in a third direction, the line of sight 744 from the phone camera 742 is able to observe the user's face, and if the user is looking in a fourth direction, the line of sight 754 from the tablet camera 752 is able to observe the user's face. If the user is looking in a fifth direction, the line of sight 764 from the wearable camera 762, which can be a device such as the glasses 760 shown and can be worn by another user or an observer, is able to observe the user's face. If the user is looking in a sixth direction, the line of sight 774 from the wearable watch-type device 770, with a camera 772 included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 710 can also use a wearable device including a camera for gathering contextual information and/or collecting expression data on other users. Because the user 710 can move her or his head, the facial data can be collected intermittently when she or he is looking in a direction of a camera. In some cases, multiple people can be included in the view from one or more cameras, and some embodiments include filtering out faces of one or more other people to determine whether the user 710 is looking toward a camera. All or some of the expression data can be continuously or sporadically available from the various devices and other devices.

The captured video data can include facial expressions, and can be analyzed on a computing device such as the video capture device or on another separate device. The analysis can take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device different from the capturing device.

Figure 8:
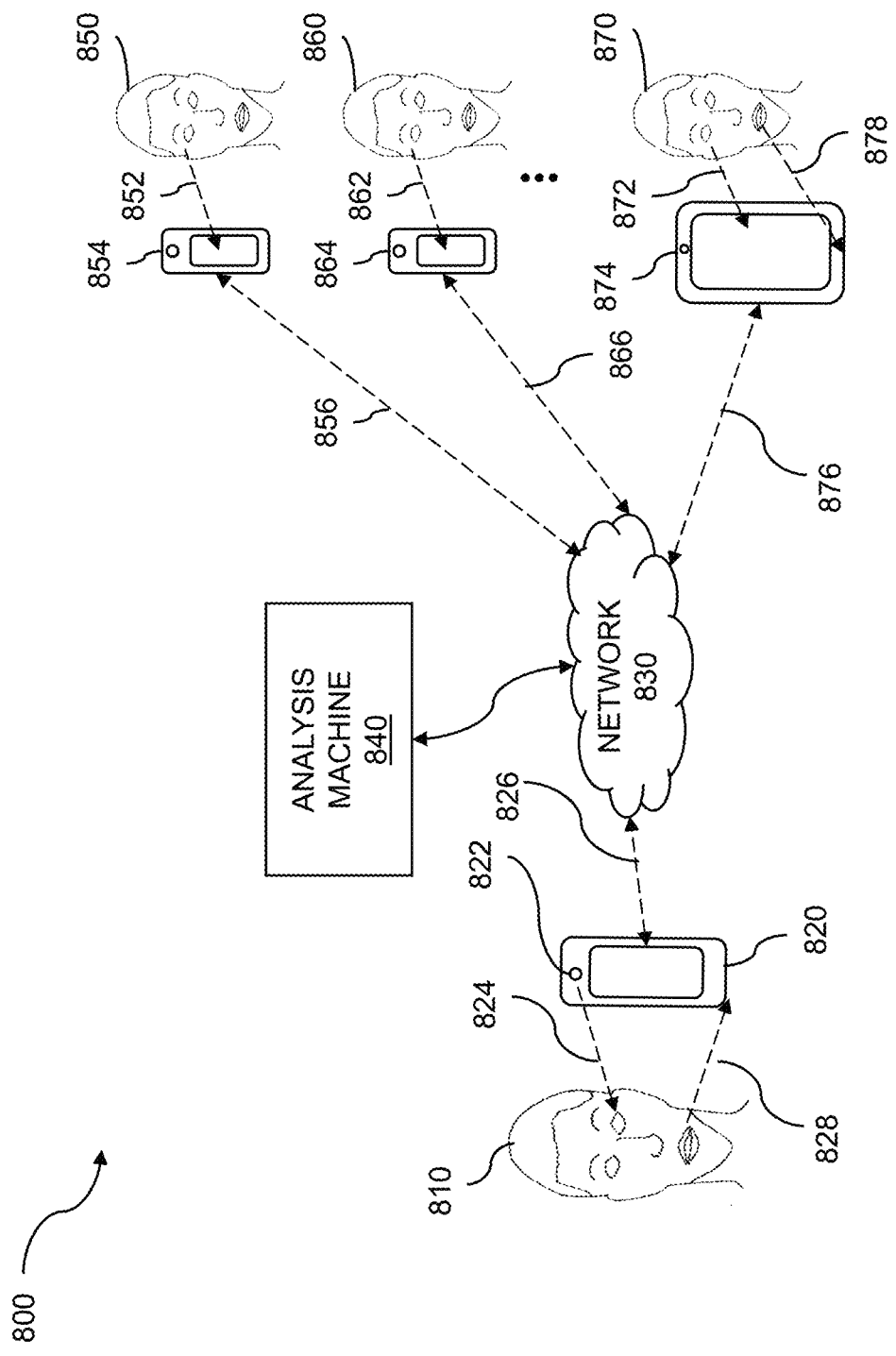
FIG. 8 illustrates live streaming of social video and audio.

FIG. 8 illustrates live streaming of social video and audio. The streaming of social video and social audio can be applied to directed control transfer for autonomous vehicles. The directed control transfer is based on a state of operation for the vehicle and a condition of an individual based on a cognitive scoring metric. The condition of the individual can include being alert, engaged, impaired, asleep, unconscious, reclined, drowsy, fatigued, inattentive, or exhibiting antisocial behavior. The streaming and analysis can be facilitated by a video capture device, an audio capture device, an infrared sensor or other sensor, a local server, a remote server, semiconductor-based logic, and so on. The streaming can be live streaming and can include cognitive state analysis, cognitive state event signature analysis, etc. Live streaming video or audio is an example of one-to-many social media, where video can be sent over a computer network such as the Internet from one person to a plurality of people using a social media app and/or platform. Live streaming is one of numerous popular techniques used by people who want to disseminate ideas, send information, provide entertainment, share experiences, and so on. Some of the live streams can be scheduled, such as webcasts, online classes, sporting events, news, computer gaming, or video conferences, while others can be impromptu streams that are broadcast as needed or when desirable. Examples of impromptu live stream videos can range from individuals simply wanting to share experiences with their social media followers to live coverage of breaking news, emergencies, or natural disasters. The latter coverage is known as mobile journalism, or "mo jo", and is becoming increasingly common. With this type of coverage, news reporters can use networked, portable electronic devices to provide mobile journalism content to a plurality of social media followers. Such reporters can be quickly and inexpensively deployed as the need or desire arises.

Several live streaming social media apps and platforms can be used for transmitting video. One such video social media app is Meerkat™ which can link with a user's Twitter™ account. Meerkat™ enables a user to stream video using a handheld, networked electronic device coupled to video capabilities. Viewers of the live stream can comment on the stream using tweets that can be seen and responded to by the broadcaster. Another popular app is Periscope™ which can transmit a live recording from one user to his or her Periscope™ account and to other followers. The Periscope™ app can be executed on a mobile device. The user's Periscope™ followers can receive an alert whenever that user begins a video transmission. Another live-stream video platform is Twitch™ which can be used for video streaming of video gaming and broadcasts of various competitions and events.

The example 800 shows a user 810 broadcasting a video live stream and an audio live stream to one or more people as shown by a first person 850, a second person 860, and a third person 870. A portable, network-enabled, electronic device 820 can be coupled to a front-facing camera 822. The portable electronic device 820 can be a smartphone, a PDA, a tablet, a laptop computer, and so on. The camera 822 coupled to the device 820 can have a line-of-sight view 824 to the user 810 and can capture video of the user 810. The portable electronic device 820 can be coupled to a microphone (not shown). The microphone can capture voice data 828 such as speech and non-speech vocalizations. In embodiments, non-speech vocalizations can include grunts, yelps, squeals, snoring, sighs, laughter, filled pauses, unfilled pauses, yawns, or the like. The captured video and audio can be sent to an analysis or recommendation machine 840 using a network link 826 to a computer network 830 such as the Internet. The network link can be a wireless link, a wired link, and so on. The recommendation machine 840 can recommend to the user 810 an app and/or platform that can be supported by the server and can be used to provide a video live stream, an audio live stream, or both a video live stream and an audio live stream to one or more followers of the user 810.

In the example 800, the user 810 has three followers: a first person 850, a second person 860, and a third person 870. Each follower has a line-of-sight view to a video screen on a portable, networked electronic device. In other embodiments, one or more followers follow the user 810 using any other networked electronic device, including a computer. In the example 800, a first person 850 has a line-of-sight view 852 to the video screen of a device 854; a second person 860 has a line-of-sight view 862 to the video screen of a device 864, and a third person 870 has a line-of-sight view 872 to the video screen of a device 874. The device 874 can also capture audio data 878 from the third person 870. The portable electronic devices 854, 864, and 874 can each be a smartphone, a PDA, a tablet, and so on. Each portable device can receive the video stream and the audio stream being broadcast by the user 810 through the network 830 using the app and/or platform that can be recommended by the recommendation machine 840. The device 854 can receive a video stream and the audio stream using the network link 856, the device 864 can receive a video stream and the audio stream using the network link 866, the device 874 can receive a video stream and the audio stream using the network link 876, and so on. The network link can be a wireless link, a wired link, a hybrid link, and so on. Depending on the app and/or platform that can be recommended by the recommendation engine 840, one or more followers, such as the followers shown 850, 860, and 870, can reply to, comment on, or otherwise provide feedback to the user 810 using their respective devices 854, 864, and 874.

The human face provides a powerful communications medium through its ability to exhibit a myriad of expressions that can be captured and analyzed for a variety of purposes. In some cases, media producers are acutely interested in evaluating the effectiveness of message delivery by video media. Such video media includes advertisements, political messages, educational materials, television programs, movies, government service announcements, etc. Automated facial analysis can be performed on one or more video frames containing a face in order to detect facial action. Based on the facial action detected, a variety of parameters can be determined, including affect valence, spontaneous reactions, facial action units, and so on. The parameters that are determined can be used to infer or predict emotional, mental, and cognitive states. For example, determined valence can be used to describe the emotional reaction of a viewer to a video media presentation or another type of presentation. Positive valence provides evidence that a viewer is experiencing a favorable emotional response to the video media presentation, while negative valence provides evidence that a viewer is experiencing an unfavorable emotional response to the video media presentation. Other facial data analysis can include the determination of discrete emotional states of the viewer or viewers.

Facial data can be collected from a plurality of people using any of a variety of cameras. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. In some embodiments, the person is permitted to "opt-in" to the facial data collection. For example, the person can agree to the capture of facial data using a personal device such as a mobile device or another electronic device by selecting an opt-in choice. Opting-in can then turn on the person's webcam-enabled device and can begin the capture of the person's facial data via a video feed from the webcam or other camera. The video data that is collected can include one or more persons experiencing an event. The one or more persons can be sharing a personal electronic device or can each be using one or more devices for video capture. The videos can be collected using a web-based framework. The web-based framework can be used to display the video media presentation or event as well as to collect videos from multiple viewers who are online. That is, the collection of videos can be crowdsourced from those viewers who elected to opt-in to the video data collection.

The videos captured from the various viewers who chose to opt-in can be substantially different in terms of video quality, frame rate, etc. As a result, the facial video data can be scaled, rotated, and otherwise adjusted to improve consistency. Human factors further contribute to the capture of the facial video data. The facial data that is captured might or might not be relevant to the video media presentation being displayed. For example, the viewer might not be paying attention, might be fidgeting, might be distracted by an object or event near the viewer, or might be otherwise inattentive to the video media presentation. The behavior exhibited by the viewer can prove challenging to analyze due to viewer actions including eating, speaking to another person or persons, speaking on the phone, etc. The videos collected from the viewers might also include other artifacts that pose challenges during the analysis of the video data. The artifacts can include items such as eyeglasses (because of reflections), eye patches, jewelry, and clothing that occludes or obscures the viewer's face. Similarly, a viewer's hair or hair covering can present artifacts by obscuring the viewer's eyes and/or face.

The captured facial data can be analyzed using the facial action coding system (FACS). The FACS seeks to define groups or taxonomies of facial movements of the human face. The FACS encodes movements of individual muscles of the face, where the muscle movements often include slight, instantaneous changes in facial appearance. The FACS encoding is commonly performed by trained observers, but can also be performed on automated, computer-based systems. Analysis of the FACS encoding can be used to determine emotions of the persons whose facial data is captured in the videos. The FACS is used to encode a wide range of facial expressions that are anatomically possible for the human face. The FACS encodings include action units (AUs) and related temporal segments that are based on the captured facial expression. The AUs are open to higher order interpretation and decision-making. These AUs can be used to recognize emotions experienced by the person who is being observed. Emotion-related facial actions can be identified using both the emotional facial action coding system (EMFACS) and the facial action coding system affect interpretation dictionary (FACSAID). For a given emotion, specific action units can be related to the emotion. For example, the emotion of anger can be related to AUs 4, 5, 7, and 23, while happiness can be related to AUs 6 and 12. Other mappings of emotions to AUs have also been previously associated. The coding of the AUs can include an intensity scoring that ranges from A (trace) to E (maximum). The AUs can be used for analyzing images to identify patterns indicative of a particular mental and/or emotional state. The AUs range in number from 0 (neutral face) to 98 (fast up-down look). The AUs include so-called main codes (inner brow raiser, lid tightener, etc.), head movement codes (head turned left, head up, etc.), eye movement codes (eyes turned left, eyes up, etc.), visibility codes (eyes not visible, entire face not visible, etc.), and gross behavior codes (sniff, swallow, etc.). Emotion scoring can be included where intensity is evaluated, and specific emotions, moods, mental states, or cognitive states can be identified.

The coding of faces identified in videos captured of people observing an event can be automated. The automated systems can detect facial AUs or discrete emotional states. The emotional states can include amusement, fear, anger, disgust, surprise, and sadness. The automated systems can be based on a probability estimate from one or more classifiers, where the probabilities can correlate with an intensity of an AU or an expression. The classifiers can be used to identify into which of a set of categories a given observation can be placed. In some cases, the classifiers can be used to determine a probability that a given AU or expression is present in a given frame of a video. The classifiers can be used as part of a supervised machine learning technique, where the machine learning technique can be trained using "known good" data. Once trained, the machine learning technique can proceed to classify new data that is captured.

The supervised machine learning models can be based on support vector machines (SVMs). An SVM can have an associated learning model that is used for data analysis and pattern analysis. For example, an SVM can be used to classify data that can be obtained from collected videos of people experiencing a media presentation. An SVM can be trained using "known good" data that is labeled as belonging to one of two categories (e.g. smile and no-smile). The SVM can build a model that assigns new data into one of the two categories. The SVM can construct one or more hyperplanes that can be used for classification. The hyperplane that has the largest distance from the nearest training point can be determined to have the best separation. The largest separation can improve the classification technique by increasing the probability that a given data point can be properly classified.

In another example, a histogram of oriented gradients (HoG) can be computed. The HoG can include feature descriptors and can be computed for one or more facial regions of interest. The regions of interest of the face can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example. The gradients can be intensity gradients and can be used to describe an appearance and a shape of a local object. The HoG descriptors can be determined by dividing an image into small, connected regions, also called cells. A histogram of gradient directions or edge orientations can be computed for pixels in the cell. Histograms can be contrast-normalized based on intensity across a portion of the image or the entire image, thus reducing any influence from differences in illumination or shadowing changes between and among video frames. The HoG can be computed on the image or on an adjusted version of the image, where the adjustment of the image can include scaling, rotation, etc. The image can be adjusted by flipping the image around a vertical line through the middle of a face in the image. The symmetry plane of the image can be determined from the tracker points and landmarks of the image.

In embodiments, an automated facial analysis system identifies five facial actions or action combinations in order to detect spontaneous facial expressions for media research purposes. Based on the facial expressions that are detected, a determination can be made with regard to the effectiveness of a given video media presentation, for example. The system can detect the presence of the AUs or the combination of AUs in videos collected from a plurality of people. The facial analysis technique can be trained using a web-based framework to crowdsource videos of people as they watch online video content. The video can be streamed at a fixed frame rate to a server. Human labelers can code for the presence or absence of facial actions including a symmetric smile, unilateral smile, asymmetric smile, and so on. The trained system can then be used to automatically code the facial data collected from a plurality of viewers experiencing video presentations (e.g. television programs).

Spontaneous asymmetric smiles can be detected in order to understand viewer experiences. Related literature indicates that as many asymmetric smiles occur on the right hemi face as do on the left hemi face, for spontaneous expressions. Detection can be treated as a binary classification problem, where images that contain a right asymmetric expression are used as positive (target class) samples and all other images as negative (non-target class) samples. Classifiers, including classifiers such as support vector machines (SVM) and random forests, perform the classification. Random forests can include ensemble-learning methods that use multiple learning algorithms to obtain better predictive performance. Frame-by-frame detection can be performed to recognize the presence of an asymmetric expression in each frame of a video. Facial points can be detected, including the top of the mouth and the two outer eye corners. The face can be extracted, cropped and warped into a pixel image of specific dimension (e.g. 96×96 pixels). In embodiments, the inter-ocular distance and vertical scale in the pixel image are fixed. Feature extraction can be performed using computer vision software such as OpenCV™. Feature extraction can be based on the use of HoGs. HoGs can include feature descriptors and can be used to count occurrences of gradient orientation in localized portions or regions of the image. Other techniques can be used for counting occurrences of gradient orientation, including edge orientation histograms, scale-invariant feature transformation descriptors, etc. The AU recognition tasks can also be performed using Local Binary Patterns (LBP) and Local Gabor Binary Patterns (LGBP). The HoG descriptor represents the face as a distribution of intensity gradients and edge directions and is robust in its ability to translate and scale. Differing patterns, including groupings of cells of various sizes and arranged in variously sized cell blocks, can be used. For example, 4×4 cell blocks of 8×8-pixel cells with an overlap of half of the block can be used. Histograms of channels can be used, including nine channels or bins evenly spread over 0-180 degrees. In this example, the HoG descriptor on a 96×96 image is 25 blocks×16 cells×9 bins=3600, the latter quantity representing the dimension. AU occurrences can be rendered. The videos can be grouped into demographic datasets based on nationality and/or other demographic parameters for further detailed analysis. This grouping and other analyses can be facilitated via semiconductor-based logic.

Figure 9:
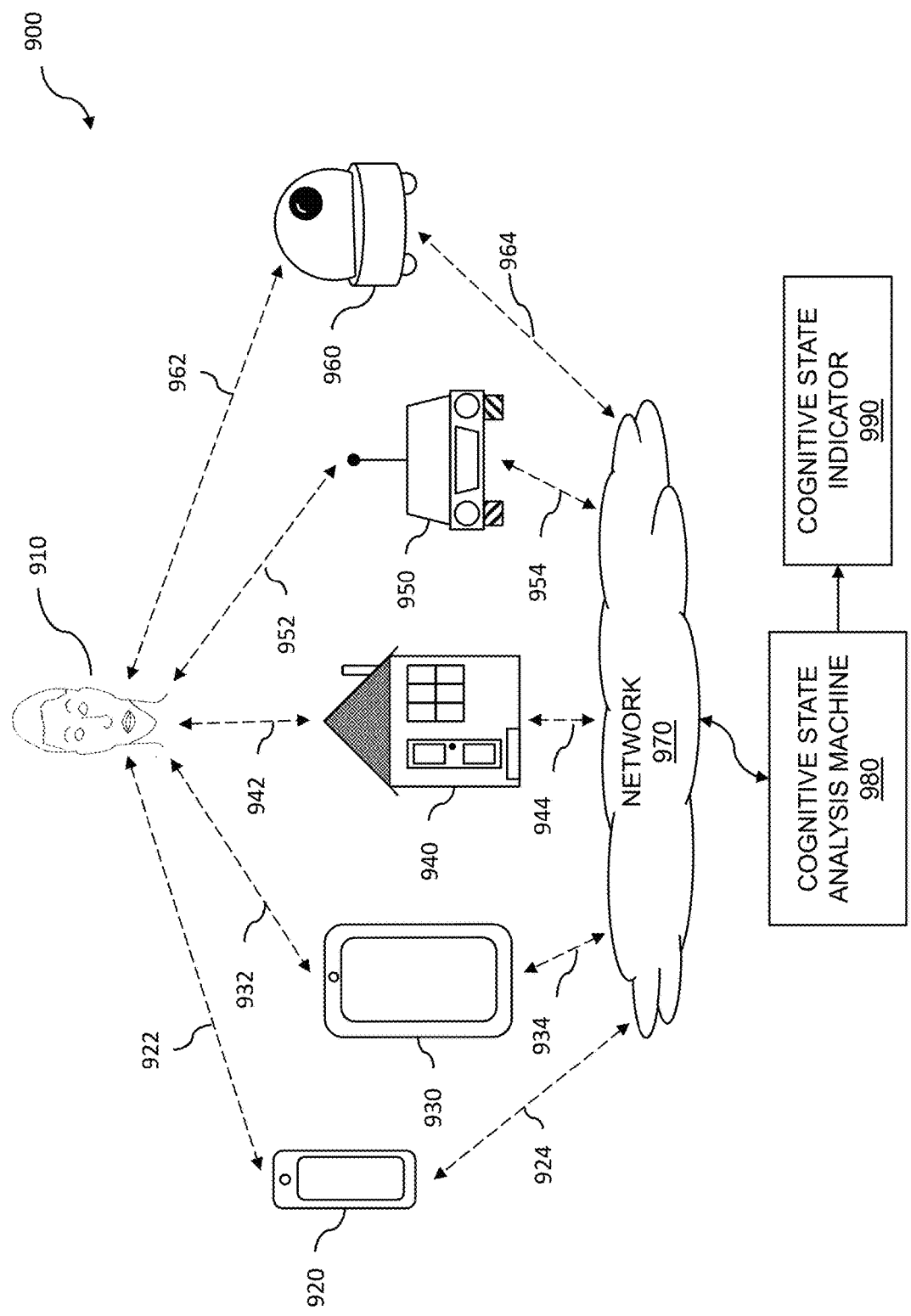
FIG. 9 shows data collection including devices and locations.

FIG. 9 shows data collection including devices and locations 900. Data, including audio data and video data, can be collected for directed control transfer for autonomous vehicles. Control can be transferred between a vehicle and an individual based on the state of operation of the vehicle, such as manual operation or autonomous operation, and the condition of the individual. The condition of the individual can include being alert, engaged, impaired, asleep, unconscious, reclined, drowsy, fatigued, inattentive, or exhibiting antisocial behavior. The multiple mobile devices, vehicles, and locations, can be used separately or in combination to collect video data on a user 910. While one person is shown, the video data can be collected on multiple people. A user 910 can be observed as she or he is performing a task, experiencing an event, viewing a media presentation, and so on. The user 910 can be shown one or more media presentations, political presentations, social media, or another form of displayed media. The one or more media presentations can be shown to a plurality of people. The media presentations can be displayed on an electronic display coupled to a client device. The data collected on the user 910 or on a plurality of users can be in the form of one or more videos, video frames, still images, etc. The plurality of videos can be of people who are experiencing different situations. Some example situations can include the user or plurality of users being exposed to TV programs, movies, video clips, social media, social sharing, and other such media. The situations could also include exposure to media such as advertisements, political messages, news programs, and so on. As noted before, video data can be collected on one or more users in substantially identical or different situations and viewing either a single media presentation or a plurality of presentations. The data collected on the user 910 can be analyzed and viewed for a variety of purposes including expression analysis, mental state analysis, cognitive state analysis, and so on. The electronic display can be on a smartphone 920 as shown, a tablet computer 930, a personal digital assistant, a television, a mobile monitor, or any other type of electronic device. In one embodiment, expression data is collected on a mobile device such as a cell phone 920, a tablet computer 930, a laptop computer, or a watch. Thus, the multiple sources can include at least one mobile device, such as a phone 920 or a tablet 930, or a wearable device such as a watch or glasses (not shown). A mobile device can include a front-facing camera and/or a rear-facing camera that can be used to collect expression data. Sources of expression data can include a webcam, a phone camera, a tablet camera, a wearable camera, and a mobile camera. A wearable camera can comprise various camera devices, such as a watch camera. In addition to using client devices for data collection from the user 910, data can be collected in a house 940 using a web camera or the like; in a vehicle 950 using a web camera, client device, etc.; by a social robot 960, and so on.

As the user 910 is monitored, the user 910 might move due to the nature of the task, boredom, discomfort, distractions, or for another reason. As the user moves, the camera with a view of the user's face can be changed. Thus, as an example, if the user 910 is looking in a first direction, the line of sight 922 from the smartphone 920 is able to observe the user's face, but if the user is looking in a second direction, the line of sight 932 from the tablet 930 is able to observe the user's face. Furthermore, in other embodiments, if the user is looking in a third direction, the line of sight 942 from a camera in the house 940 is able to observe the user's face, and if the user is looking in a fourth direction, the line of sight 952 from the camera in the vehicle 950 is able to observe the user's face. If the user is looking in a fifth direction, the line of sight 962 from the social robot 960 is able to observe the user's face. If the user is looking in a sixth direction, a line of sight from a wearable watch-type device, with a camera included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The sensor can include an infrared imaging sensor. The user 910 can also use a wearable device including a camera for gathering contextual information and/or collecting expression data on other users. Because the user 910 can move her or his head, the facial data can be collected intermittently when she or he is looking in a direction of a camera. In some cases, multiple people can be included in the view from one or more cameras, and some embodiments include filtering out faces of one or more other people to determine whether the user 910 is looking toward a camera. All or some of the expression data can be continuously or sporadically available from the various devices and other devices.

The captured video data can include facial expressions and can be transferred over a computer network 970 such as the Internet or other computer network. The smartphone 920 can share video using a link 924, the tablet 930 using a link 934, the house 940 using a link 944, the vehicle 950 using a link 954, and the social robot 960 using a link 964. The links 924, 934, 944, 954, and 964 can be wired, wireless, and hybrid links. The captured video data, including facial expressions, can be analyzed on a cognitive state analysis machine 980, on a computing device such as the video capture device, or on another separate device. The analysis could take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capture device. The analysis data from the cognitive state analysis machine can be processed by a cognitive state indicator 990. The cognitive state indicator 990 can indicate cognitive states, mental states, moods, emotions, etc. In embodiments, the emotions can include of one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, sadness, poignancy, or mirth.

Figure 10:
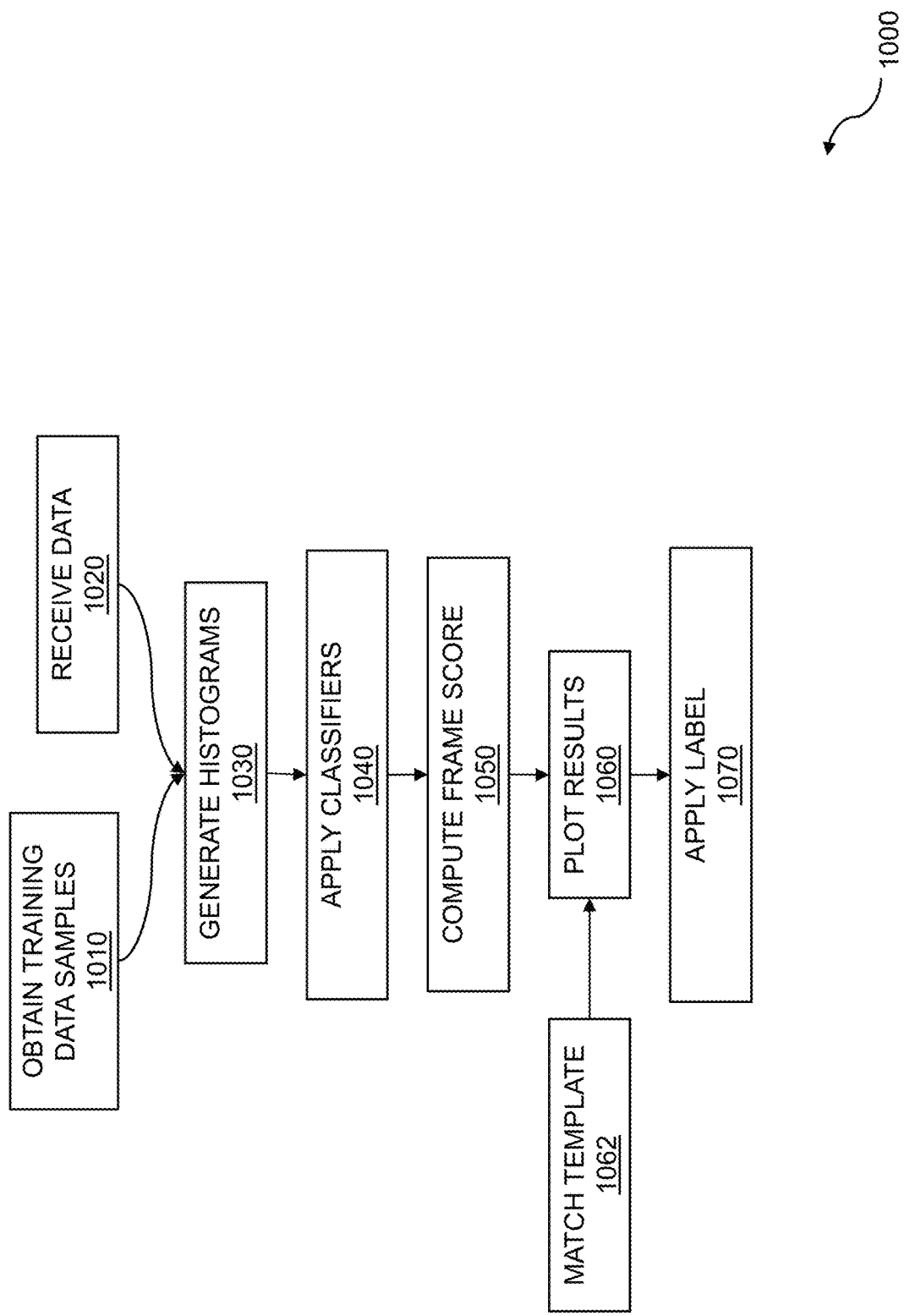
FIG. 10 is a flow diagram for detecting expressions.

FIG. 10 is a flow diagram for detecting expressions. Detecting expressions can be performed for directed control transfer for autonomous vehicles. Cognitive state data can be collected for an individual and analyzed to produce cognitive state information. The cognitive state information is scored to produce a cognitive scoring metric, and a condition of the individual is evaluated based on the cognitive scoring metric. Control can be transferred between the vehicle and the individual based on a state of vehicle operation and the condition of the individual. The flow 1000, or portions thereof, can be implemented in semiconductor logic, can be accomplished using a mobile device, can be accomplished using a server device, and so on. The flow 1000 can be used to automatically detect a wide range of facial expressions. A facial expression can produce strong emotional signals that can indicate valence and discrete emotional states. The discrete emotional states can include contempt, doubt, defiance, happiness, fear, anxiety, and so on. The detection of facial expressions can be based on the location of facial landmarks. The detection of facial expressions can be based on determination of action units (AU), where the action units are determined using FACS coding. The AUs can be used separately or in combination to identify facial expressions. Based on the facial landmarks, one or more AUs can be identified by number and intensity. For example, AU12 can be used to code a lip corner puller which can further be used to infer a smirk.

The flow 1000 begins by obtaining training image data samples 1010. The image samples can include a plurality of images of one or more people. Human coders who are trained to correctly identify AU codes based on the FACS can code the images. The training or "known good" images can be used as a basis for training a machine learning technique. Once trained, the machine learning technique can be used to identify AUs in other images that can be collected using a camera, a sensor, and so on. The flow 1000 continues with receiving image data 1020. The image data 1020 can be received from a camera, a sensor, and so on. A sensor can include an infrared imaging sensor. As previously discussed, the camera or cameras can include a webcam, where a webcam can include a video camera, a still camera, a thermal imager, an infrared imaging sensor, a CCD device, a phone camera, a three-dimensional camera, a depth camera, a light field camera, multiple webcams used to show different views of a person, or any other type of image capture apparatus that can allow captured data to be used in an electronic system. The image that is received can be manipulated in order to improve the processing of the image. For example, the image can be cropped, scaled, stretched, rotated, flipped, etc. in order to obtain a resulting image that can be analyzed more efficiently. Multiple versions of the same image can be analyzed. In some cases, the manipulated image and a flipped or mirrored version of the manipulated image can be analyzed alone and/or in combination to improve analysis. The flow 1000 continues with generating histograms 1030 for the training images and the one or more versions of the received image. The histograms can be based on a HoG or another histogram. As described in previous paragraphs, the HoG can include feature descriptors and can be computed for one or more regions of interest in the training images and the one or more received images. The regions of interest in the images can be located using facial landmark points, where the facial landmark points can include outer edges of nostrils, outer edges of the mouth, outer edges of eyes, etc. A HoG for a given region of interest can count occurrences of gradient orientation within a given section of a frame from a video.

The flow 1000 continues with applying classifiers 1040 to the histograms. The classifiers can be used to estimate probabilities, where the probabilities can correlate with an intensity of an AU or an expression. In some embodiments, the choice of classifiers used is based on the training of a supervised learning technique to identify facial expressions. The classifiers can be used to identify into which of a set of categories a given observation can be placed. The classifiers can be used to determine a probability that a given AU or expression is present in a given image or frame of a video. In various embodiments, the one or more AUs that are present include AU01 inner brow raiser, AU12 lip corner puller, AU38 nostril dilator, and so on. In practice, the presence or absence of multiple AUs can be determined. The flow 1000 continues with computing a frame score 1050. The score computed for an image, where the image can be a frame from a video, can be used to determine the presence of a facial expression in the image or video frame. The score can be based on one or more versions of the image or a manipulated image. The score can be based on a comparison of the manipulated image to a flipped or mirrored version of the manipulated image. The score can be used to predict a likelihood that one or more facial expressions are present in the image. The likelihood can be based on computing a difference between the outputs of a classifier used on the manipulated image and on the flipped or mirrored image, for example. The classifier that is used can identify symmetrical facial expressions (e.g. smile), asymmetrical facial expressions (e.g. outer brow raiser), and so on.

The flow 1000 continues with plotting results 1060. The results that are plotted can include one or more scores for one or more frames computed over a given time t. For example, the plotted results can include classifier probability results from analysis of HoGs for a sequence of images and video frames. The plotted results can be matched with a template 1062. The template can be temporal and can be represented by a centered box function or another function. A best fit with one or more templates can be found by computing a minimum error. Other best-fit techniques can include polynomial curve fitting, geometric curve fitting, and so on. The flow 1000 continues with applying a label 1070. The label can be used to indicate that a particular facial expression has been detected in the one or more images or video frames which constitute the image data that was received 1020. The label can be used to indicate that any of a range of facial expressions has been detected, including a smile, an asymmetric smile, a frown, and so on. Various steps in the flow 1000 may be changed in order, repeated, omitted, or the like without departing from the disclosed concepts. Various embodiments of the flow 1000 can be included in a computer program product embodied in a non-transitory computer readable medium that includes code executable by one or more processors. Various embodiments of the flow 1000, or portions thereof, can be included on a semiconductor chip and implemented in special purpose logic, programmable logic, and so on.

Figure 11:
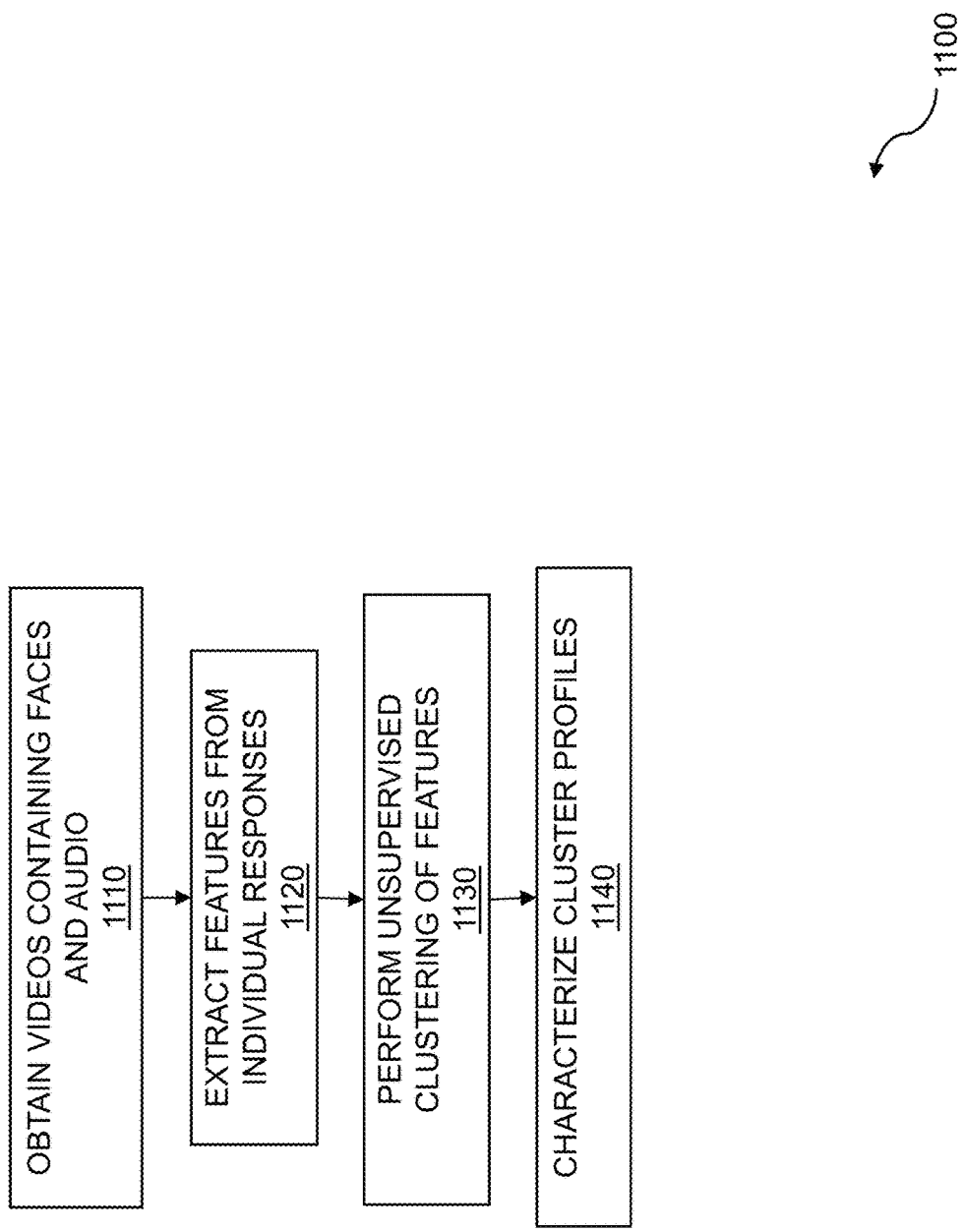
FIG. 11 is a flow diagram for the large-scale clustering of events.

FIG. 11 is a flow diagram for the large-scale clustering of events. The large-scale clustering of events can be performed for directed control transfer for autonomous vehicles. An individual can be scored based on analyzed cognitive state data to produce a cognitive scoring metric. The individual is evaluated based on the cognitive scoring metric. Control of an autonomous vehicle can be transferred between the vehicle and the individual based on a state of operation for the vehicle and the condition of the individual. The large-scale clustering of events such as facial events can be performed for data collected from a remote computing device. The facial events can be collected from people as they interact with a computer network such as the Internet. The clustering and evaluation of facial events can be augmented using a mobile device, a server, semiconductor-based logic, and so on. As discussed above, collection of facial video data from one or more people can include a web-based framework. The web-based framework can be used to collect facial video data from large numbers of people located over a wide geographic area. The web-based framework can include an opt-in feature that allows people to agree to facial data collection. The web-based framework can be used to render and display data to one or more people and can collect data from the one or more people. For example, the facial data collection can be based on showing one or more viewers a video media presentation through a website. The web-based framework can be used to display the video media presentation or event and to collect videos from multiple viewers who are online. That is, the collection of videos can be crowdsourced from those viewers who elected to opt-in to the video data collection. The video event can be a commercial, a political ad, an educational segment, and so on.

The flow 1100 includes obtaining videos containing faces with audio 1110. The videos can be obtained using one or more cameras, where the cameras can include a webcam coupled to one or more devices employed by the one or more people using the web-based framework. In-vehicle sensors can be used to collect data further to the video data and the audio data. In embodiments, the in-vehicle sensors can include one or more infrared imaging sensors. The flow 1100 continues with extracting features from the individual responses 1120. The individual responses can include videos containing faces observed by the one or more webcams. The features that are extracted can include facial features such as an eyebrow, a nostril, an eye edge, a mouth edge, and so on. The feature extraction can be based on facial coding classifiers, where the facial coding classifiers output a probability that a specified facial action has been detected in a given video frame. The flow 1100 continues with performing unsupervised clustering of features 1130. The unsupervised clustering can be based on an event. The unsupervised clustering can be based on a K-Means, where the K of the K-Means can be computed using a Bayesian Information Criterion (BICk), for example, to determine the smallest value of K that meets system requirements. Any other criterion for K can be used. The K-Means clustering technique can be used to group one or more events into various respective categories.

The flow 1100 includes characterizing cluster profiles 1140. The profiles can include a variety of facial expressions such as smiles, asymmetric smiles, eyebrow raisers, eyebrow lowerers, etc. The profiles can be related to a given event. For example, a humorous video can be displayed in the web-based framework and the video data of people who have opted-in can be collected. The characterization of the collected and analyzed video can depend in part on the number of smiles that occurred at various points throughout the humorous video. Similarly, the characterization can be performed on collected and analyzed videos of people viewing a news presentation. The characterized cluster profiles can be further analyzed based on demographic data. The number of smiles resulting from people viewing a humorous video can be compared across various demographic groups, where the groups can be formed based on geographic location, age, ethnicity, gender, and so on.

The flow 1100 can include determining cognitive state event temporal signatures. The cognitive state event temporal signatures can include information on rise time to facial expression intensity, fall time from facial expression intensity, duration of a facial expression, and so on. In some embodiments, the cognitive state event temporal signatures are associated with certain demographics, ethnicities, cultures, etc. The cognitive state event temporal signatures can be used to identify one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. Various steps in the flow 1100 may be changed in order, repeated, omitted, or the like without departing from the disclosed concepts. Various embodiments of the flow 1100 can be included in a computer program product embodied in a non-transitory computer readable medium that includes code executable by one or more processors. Various embodiments of the flow 1100, or portions thereof, can be included on a semiconductor chip and implemented in special purpose logic, programmable logic, and so on.

Figure 12:
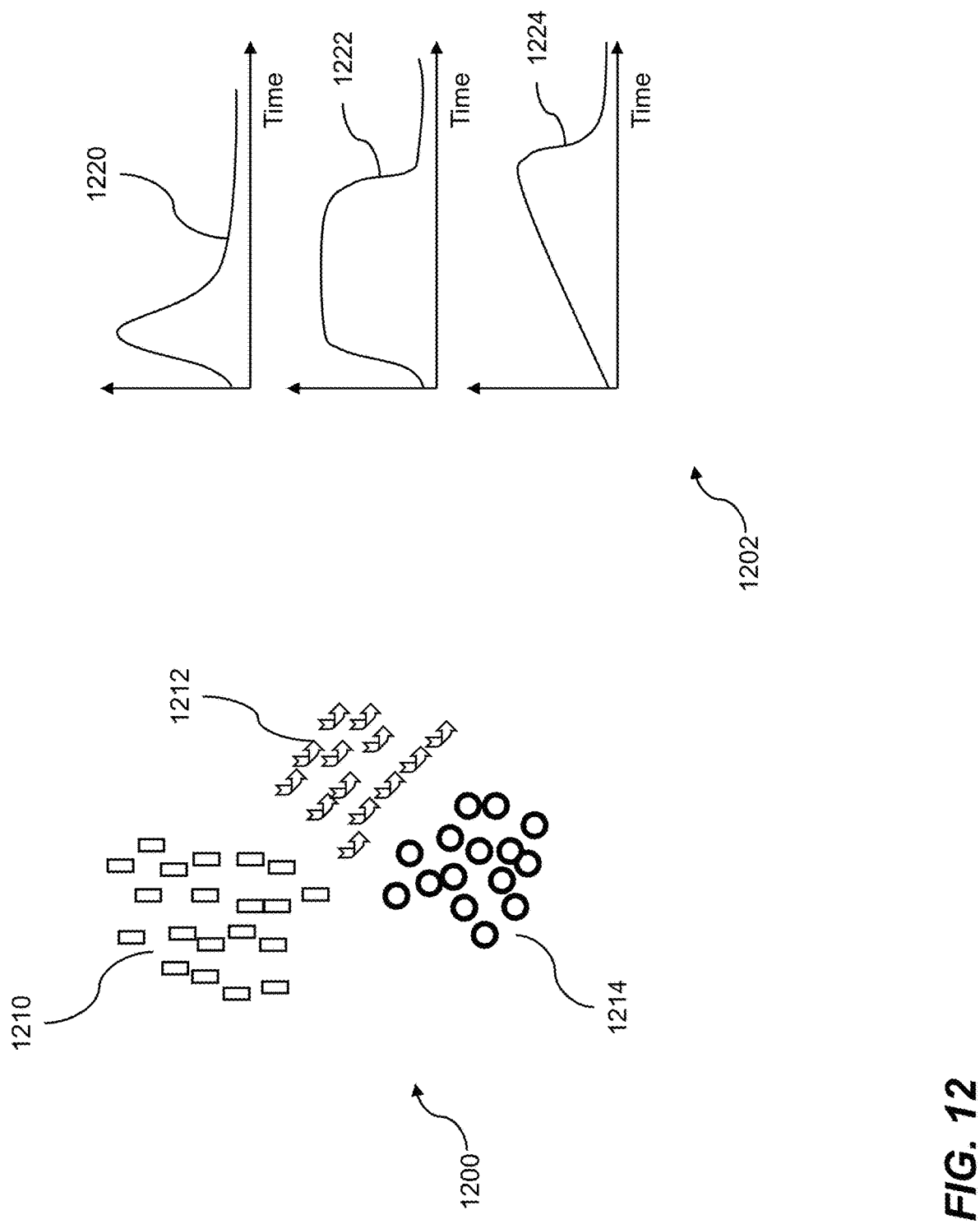
FIG. 12 is an example illustrating unsupervised clustering of features and characterizations of cluster profiles.

FIG. 12 is an example illustrating unsupervised clustering of features and characterizations of cluster profiles. The clustering of features and characterizations of cluster profiles can be performed for directed control transfer for autonomous vehicles. Transfer of control between an autonomous vehicle and an individual can be performed based on both a state of operation of the vehicle and a condition of the individual. The condition of the individual is based on a cognitive scoring metric. The example 1200 shows three clusters, 1210, 1212, and 1214. The clusters can be based on video collected from people who have opted-in to video collection. When the data collected is captured using a web-based framework, the data collection can be extensive, including hundreds, thousands, or even more participants who can be situated locally and/or across a wide geographic area. Unsupervised clustering is a technique that can be used to process the large amounts of captured facial data, audio data, or infrared data, and to identify groupings of similar observations. The unsupervised clustering can also be used to characterize the groups of similar observations. The characterizations can include identifying behaviors of the participants. The characterizations can be based on identifying facial expressions and facial action units of the participants. Some behaviors and facial expressions can include faster or slower onsets, faster or slower offsets, longer or shorter durations, etc. The onsets, offsets, and durations can all correlate to time. The data clustering that results from the unsupervised clustering can support data labeling. The labeling can include FACS coding. The clusters can be partially or totally based on a facial expression resulting from participants viewing a video presentation, where the video presentation can be an advertisement, a political message, educational material, a public service announcement, and so on. The clusters can be correlated with demographic information, where the demographic information can include educational level, geographic location, age, gender, income level, and so on.

The cluster profiles 1202 can be generated based on the clusters that can be formed from unsupervised clustering, with time shown on the x-axis and intensity or frequency shown on the y-axis. The cluster profiles can be based on captured facial data, including facial expressions. The first cluster profile 1220 can be based on the first cluster 1210, the second cluster profile 1222 can be based on the second cluster 1212, and the third cluster profile 1224 can be based on the third cluster 1214. The cluster profiles 1220, 1222, and 1224 can pertain to smiles, smirks, frowns, or any other facial expression. The emotional states of the people who have opted-in to video collection can be inferred by analyzing the clustered facial expression data. The cluster profiles can be plotted with respect to time and can show a rate of onset, a duration, and an offset (rate of decay). Other time-related factors can be included in the cluster profiles. The cluster profiles can be correlated with demographic information, as described above.

Figure 13:
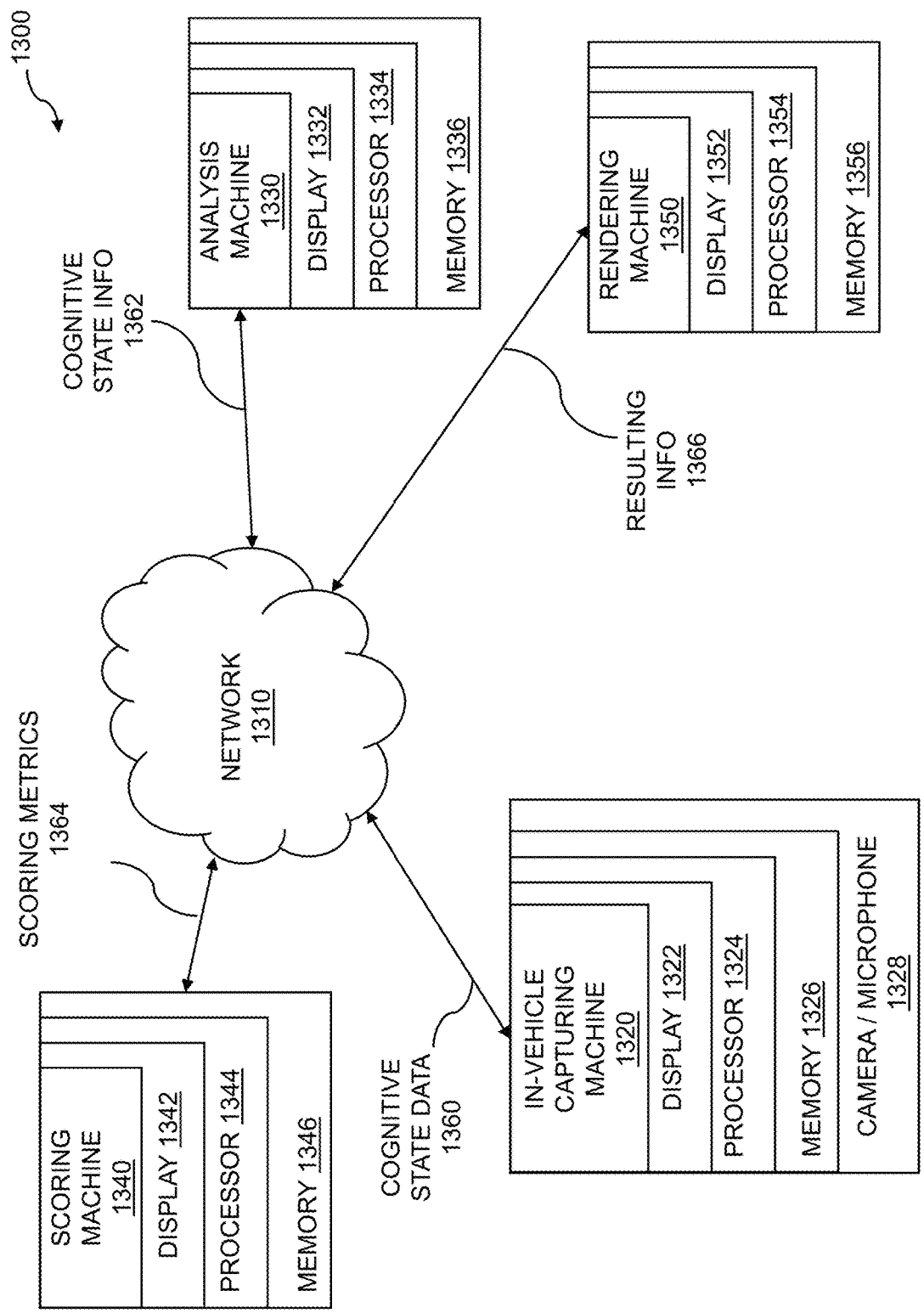
FIG. 13 is a diagram of a system for an emotion-enabled avatar for animating emotions.

FIG. 13 is a diagram of a system for directed control transfer for autonomous vehicles. Cognitive state data is collected for an individual who is within a vehicle. The vehicle has both an autonomous mode of operation and a manual mode of operation. The cognitive state data collected from the individual is analyzed to produce cognitive state information, from which a cognitive metric can be scored. Based on determining both an operation state for the vehicle and the condition of the individual, control can be transferred between the vehicle and the individual. The system 1300 includes a network 1310. The network can include an on-vehicle network, access to the Internet, an intranet, or another wired, wireless, or hybrid computer network. The network can be used for communication among the various machines that comprise a system for cognitive analysis. An in-vehicle capturing machine 1320 has a memory 1326, which stores instructions, and one or more processors 1324 attached to the memory 1326, wherein the one or more processors 1324 can execute instructions. The in-vehicle capturing machine 1320 can also have a network connection to carry cognitive state data 1360. The cognitive state data can include audio data, video data, or infrared data. The in-vehicle capturing machine can include a display 1322 that can present various data to a user. The in-vehicle capturing machine 1320 can collect audio data, video data, infrared data, and cognitive state data from a plurality of people as they interact with a vehicle or are engaged in an activity such as a social activity including traveling in the vehicle. The in-vehicle capturing machine 1320 can include a camera and microphone 1328. The camera 1328 can include a webcam, a video camera, a still camera, a thermal imager, an infrared camera, a CCD device, a phone camera, a three-dimensional camera, a depth camera, a light field camera, multiple webcams used to show different views of a person, or any other type of image capture technique that can allow captured data to be used in an electronic system. In some embodiments, there are multiple in-vehicle capturing machines 1320 that each collect cognitive state data including audio data, video data, or infrared data from one person or a plurality of people as they interact with a vehicle or are engaged in a social activity. The in-vehicle capturing machine 1320 can communicate with an analysis machine 1330 and other machines over the network 1310, some other computer network, or by another method suitable for communication between and among computers. In some embodiments, the analysis machine 1330 functionality is embodied in the in-vehicle capturing machine 1320.

A scoring machine 1340 can have a network connection for scoring metrics and other data 1364, a memory 1346, which stores instructions, and one or more processors 1344 attached to the memory 1346, wherein the one or more processors 1344 can execute instructions. The scoring machine 1340 can score an individual based on cognitive state data, cognitive state information, and so on. The scoring can include producing a cognitive scoring metric. The cognitive scoring metrics can be determined for one or more individuals interacting with one or more in-vehicle capturing machines 1320. In some embodiments, the scoring machine 1340 renders content on a display 1342. The display 1342 can be any electronic display, including but not limited to, a computer display, a laptop screen, a netbook screen, a tablet computer screen, a smartphone display, a mobile device display, a remote with a display, a television, a projector, or the like.

An analysis machine 1330 can have a network connection for individual cognitive state information 1362, a memory 1336, which stores instructions, and one or more processors 1334 attached to the memory 1336, wherein the one or more processors 1334 can execute instructions. The analysis machine 1330 can receive individual cognitive state information 1362 collected from one or more people as they interact with a vehicle, social activity, etc., on an in-vehicle capturing machine 1320 and can analyze, score, etc., the cognitive state information on the plurality of people who interact with a vehicle, social activity, etc. In some embodiments, the analysis machine 1330 also allows a user to view and evaluate on a display 1332 the individual cognitive state information that is associated with the individual within a vehicle, a social activity, and the like.

A rendering machine 1350 can have a memory 1356, which stores instructions, and one or more processors 1354 attached to the memory 1356, wherein the one or more processors 1354 can execute instructions. The rendering machine 1350 can use a network connection, or another computer communication technique, to send and receive resulting information 1366. The rendering machine 1350 can receive cognitive state information 1360, audio information, video information including facial information, infrared information, scoring metrics 1364, individual cognitive state information 1362, etc. The data and information can be rendered on a display 1352.

In other embodiments, the system 1300 can include a computer program product embodied in a non-transitory computer readable medium for cognitive analysis, the computer program product comprising code which causes one or more processors to perform operations of: collecting, by in-vehicle sensors, cognitive state data for an individual within a vehicle which has an autonomous mode of operation; analyzing, using one or more processors, the cognitive state data collected from the individual to produce cognitive state information; scoring the individual based on the cognitive state information to produce a cognitive scoring metric; determining a state of operation for the vehicle; evaluating a condition of the individual based on the cognitive scoring metric; and transferring control between the vehicle and the individual based on the state of operation of the vehicle and the condition of the individual.

Each of the above methods may be executed on one or more processors on one or more computer systems. Embodiments may include various forms of distributed computing, client/server computing, and cloud-based computing. Further, it will be understood that for each flow chart in this disclosure, the depicted steps or boxes are provided for purposes of illustration and explanation only. The steps may be modified, omitted, or re-ordered and other steps may be added without departing from the scope of this disclosure. Further, each step may contain one or more sub-steps. While the foregoing drawings and description set forth functional aspects of the disclosed systems, no particular arrangement of software and/or hardware for implementing these functional aspects should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. Each element of the block diagrams and flowchart illustrations, as well as each respective combination of elements in the block diagrams and flowchart illustrations, illustrates a function, step or group of steps of the methods, apparatus, systems, computer program products and/or computer-implemented methods. Any and all such functions may be implemented by computer program instructions, by special-purpose hardware-based computer systems, by combinations of special purpose hardware and computer instructions, by combinations of general purpose hardware and computer instructions, and so on. Any and all of these may be generally referred to herein as a "circuit," "module," or "system."

A programmable apparatus which executes any of the above-mentioned computer program products or computer implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are not limited to applications involving conventional computer programs or programmable apparatus that run them. It is contemplated, for example, that embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized. The computer readable medium may be a non-transitory computer readable medium for storage. A computer readable storage medium may be electronic, magnetic, optical, electromagnetic, infrared, semiconductor, or any suitable combination of the foregoing. Further computer readable storage medium examples may include an electrical connection having one or more wires, a portable computer diskette, a hard disk, a random-access memory (RAM), a read-only memory (ROM), an erasable programmable read-only memory (EPROM, Flash, MRAM, FeRAM, or phase change memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more threads. Each thread may spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States, then the method is considered to be performed in the United States by virtue of the entity causing the step to be performed.

While the invention has been disclosed in connection with preferred embodiments shown and described in detail, various modifications and improvements thereon will become apparent to those skilled in the art. Accordingly, the spirit and scope of the present invention is not to be limited by the foregoing examples, but is to be understood in the broadest sense allowable by law.

What is claimed is:

1. A computer-implemented method for cognitive analysis comprising:
   collecting, by in-vehicle sensors, cognitive state data for an individual within a vehicle which has an autonomous mode of operation;
   analyzing, using one or more processors, the cognitive state data collected from the individual to produce cognitive state information;
   scoring the individual based on the cognitive state information to produce a cognitive scoring metric;
   determining a state of operation for the vehicle;
   evaluating a condition of the individual based on the cognitive scoring metric, wherein the evaluating the condition of the individual is based on machine learning, wherein the machine learning includes learning layers and weights for a deep learning network, and wherein the machine learning is tailored for the individual, and wherein the machine learning is based on a profile for the individual, and wherein the deep learning network includes a convolutional neural network, wherein the convolutional neural network is trained for voice characteristics;
   transferring control between the vehicle and the individual based on the state of operation of the vehicle and the condition of the individual; and
   sharing results of the machine learning with a second vehicle.

2. The method of claim 1 wherein the cognitive state data includes facial image data from the individual.

3. The method of claim 2 wherein the in-vehicle sensors include a plurality of cameras to capture a multiplicity of views.

4. The method of claim 3 wherein the multiplicity of views allows for facial occlusion by one camera from the plurality of cameras.

5. The method of claim 1 wherein the cognitive state data includes audio data from the individual.

6. The method of claim 5 wherein the audio data includes voice data from the individual.

7. The method of claim 6 wherein the voice data includes non-speech vocalizations.

8. The method of claim 7 wherein the non-speech vocalizations include grunts, yelps, squeals, snoring, sighs, laughter, filled pauses, unfilled pauses, or yawns.

9. The method of claim 1 wherein the cognitive state data includes biosensor data from the individual.

10. The method of claim 1 wherein the transferring control includes transfer of control for the vehicle from the individual to the vehicle in the autonomous mode.

11. The method of claim 1 wherein the transferring control includes transfer of control for the vehicle from the vehicle in the autonomous mode to the individual.

12. The method of claim 1 wherein the condition of the individual includes being alert, engaged, impaired, asleep, unconscious, reclined, drowsy, fatigued, inattentive, or exhibiting antisocial behavior.

13. The method of claim 1 wherein the cognitive scoring metric includes a numeric representation for a mental state.

14. The method of claim 13 wherein the numeric representation includes a probability for occurrence of the mental state.

15. The method of claim 1 wherein the cognitive state information includes a subset of the cognitive state data, a summary of the cognitive state data, or an analysis of the cognitive state data.

16. The method of claim 1 wherein the machine learning is initiated based on a demographic for the individual.

17. The method of claim 16 wherein a set of layers and weights is used as an initial point based on the demographic for the individual.

18. The method of claim 1 further comprising performing facial recognition on the individual.

19. The method of claim 1 further comprising performing voice recognition on the individual.

20. The method of claim 1 wherein the in-vehicle sensors include one or more infrared imaging sensors.

21. A computer program product embodied in a non-transitory computer readable medium for cognitive analysis, the computer program product comprising code which causes one or more processors to perform operations of:
   collecting, by in-vehicle sensors, cognitive state data for an individual within a vehicle which has an autonomous mode of operation;
   analyzing, using one or more processors, the cognitive state data collected from the individual to produce cognitive state information;
   scoring the individual based on the cognitive state information to produce a cognitive scoring metric;
   determining a state of operation for the vehicle;
   evaluating a condition of the individual based on the cognitive scoring metric, wherein the evaluating the condition of the individual is based on machine learning, wherein the machine learning includes learning layers and weights for a deep learning network, and wherein the machine learning is tailored for the individual, and wherein the machine learning is based on a profile for the individual, and wherein the deep learning network includes a convolutional neural network, wherein the convolutional neural network is trained for voice characteristics;
   transferring control between the vehicle and the individual based on the state of operation of the vehicle and the condition of the individual; and
   sharing results of the machine learning with a second vehicle.

22. A computer system for cognitive analysis comprising:
   a memory which stores instructions;
   one or more processors attached to the memory wherein the one or more processors, when executing the instructions which are stored, are configured to:
      collect, by in-vehicle sensors, cognitive state data for an individual within a vehicle which has an autonomous mode of operation;
      analyze, using one or more processors, the cognitive state data collected from the individual to produce cognitive state information;
      score the individual based on the cognitive state information to produce a cognitive scoring metric;
      determine a state of operation for the vehicle;
      evaluate a condition of the individual based on the cognitive scoring metric using machine learning, wherein the machine learning includes learning layers and weights for a deep learning network, and wherein the machine learning is tailored for the individual, and wherein the machine learning is based on a profile for the individual, and wherein the deep learning network includes a convolutional neural network, and wherein the convolutional neural network is trained for voice characteristics;

transfer control between the vehicle and the individual based on the state of operation of the vehicle and the condition of the individual; and share results of the machine learning with a second vehicle.

23. The method of claim 1 wherein the profile for the individual includes at least one of vehicle preferences, vehicle settings, preferred transportation modes, routes, and times for commuting.

24. The method of claim 17 wherein the set of layers and weights is derived from collaborative filtering.

25. A computer-implemented method for cognitive analysis comprising:

collecting, by in-vehicle sensors, cognitive state data for an individual within a vehicle which has an autonomous mode of operation;

analyzing, using one or more processors, the cognitive state data collected from the individual to produce cognitive state information;

scoring the individual based on the cognitive state information to produce a cognitive scoring metric;

determining a state of operation for the vehicle;

evaluating a condition of the individual based on the cognitive scoring metric, wherein the evaluating the condition of the individual is based on machine learning, wherein the machine learning includes learning layers and weights for a deep learning network, and wherein the machine learning is tailored for the individual, and wherein the machine learning is based on a profile for the individual, wherein the profile for the individual includes at least one of vehicle preferences, vehicle settings, preferred transportation modes, routes, and times for commuting, wherein the machine learning is initiated based on a demographic for the individual, wherein a set of layers and weights is used as an initial point based on the demographic for the individual, wherein the set of layers and weights is derived from collaborative filtering, and wherein the deep learning network includes a convolutional neural network, wherein the convolutional neural network is trained for voice characteristics; and transferring control between the vehicle and the individual based on the state of operation of the vehicle and the condition of the individual.

* * * * *